(12) United States Patent
Ohishi

(10) Patent No.: US 11,273,326 B2
(45) Date of Patent: Mar. 15, 2022

(54) RADIOTHERAPY SYSTEM AND TREATMENT SUPPORT APPARATUS

(71) Applicant: Canon Medical Systems Corporation, Otawara (JP)

(72) Inventor: Satoru Ohishi, Otawara (JP)

(73) Assignee: Canon Medical Systems Corporation, Otawara (JP)

(*) Notice: Subject to any disclaimer, the term of this patent is extended or adjusted under 35 U.S.C. 154(b) by 0 days.

(21) Appl. No.: 16/020,254

(22) Filed: Jun. 27, 2018

(65) Prior Publication Data

US 2019/0001155 A1    Jan. 3, 2019

(30) Foreign Application Priority Data

Jun. 29, 2017    (JP) .............................. JP2017-127807
Jun. 26, 2018    (JP) .............................. JP2018-120610

(51) Int. Cl.
*A61N 5/10*    (2006.01)

(52) U.S. Cl.
CPC .............. *A61N 5/1049* (2013.01); *A61N 5/10* (2013.01); *A61N 5/103* (2013.01); *A61N 5/107* (2013.01); *A61N 5/1031* (2013.01); *A61N 5/1048* (2013.01); *A61N 5/1069* (2013.01); *A61N 5/1075* (2013.01); *A61N 5/1039* (2013.01);
(Continued)

(58) Field of Classification Search
CPC ...... A61N 5/10; A61N 5/1048; A61N 5/1049; A61N 2005/105; A61N 2005/1056; A61N 2005/1059; A61N 2005/1061; A61N 5/1069; A61N 5/107; A61N 2005/1074;
(Continued)

(56) References Cited

U.S. PATENT DOCUMENTS 5,651,043 A * 7/1997 Tsuyuki ............... A61N 5/1042
378/65
6,222,544 B1 * 4/2001 Tarr ....................... A61N 5/103
128/845

(Continued)

FOREIGN PATENT DOCUMENTS

JP    11-197259    7/1999
JP    2005-27743    2/2005
(Continued)

OTHER PUBLICATIONS

Japanese Office Action dated Jan. 4, 2022 in Japanese Application No. 2018-120610, 8 pgs.

*Primary Examiner* — Allen C. Ho
(74) *Attorney, Agent, or Firm* — Oblon, McClelland, Maier & Neustadt, L.L.P.

(57) ABSTRACT

According to one embodiment, the radiotherapy system includes a medical image collecting device, a body surface data collecting device and processing circuitry. The medical image collecting device collects medical three-dimensional image data of the patient at the time of treatment planning. The body surface data collecting device collects body surface data representing a three-dimensional body surface of the patient at the time of treatment planning. The processing circuitry may generate integrated data in which at least one of the medical three-dimensional image data and the treatment target region data included in the medical three-dimensional image data, and the body surface data are integrated into an identical three-dimensional coordinate system.

24 Claims, 18 Drawing Sheets

(52) U.S. Cl.
CPC .............................. *A61N 2005/105* (2013.01);
*A61N 2005/1054* (2013.01); *A61N 2005/1056* (2013.01); *A61N 2005/1059* (2013.01); *A61N 2005/1061* (2013.01); *A61N 2005/1074* (2013.01); *A61N 2005/1076* (2013.01)

(58) Field of Classification Search
CPC .......... A61N 5/1075; A61N 2005/1076; A61N 2005/1054
USPC ......................................................... 378/65
See application file for complete search history.

(56) References Cited

U.S. PATENT DOCUMENTS

| | | | | |
|---|---|---|---|---|
| 6,535,574 | B1* | 3/2003 | Collins ................ | A61N 5/1049 378/20 |
| 6,621,889 | B1* | 9/2003 | Mostafavi ............ | A61N 5/1048 378/65 |
| 6,690,965 | B1* | 2/2004 | Riaziat .................. | A61B 6/463 600/428 |
| 6,796,943 | B2* | 9/2004 | Mochizuki ........... | A61B 5/6843 600/429 |
| 6,865,253 | B2* | 3/2005 | Blumhofer ............ | A61B 6/547 378/205 |
| 7,016,522 | B2* | 3/2006 | Bani-Hashemi ........ | A61B 6/04 250/363.04 |
| 7,221,733 | B1* | 5/2007 | Takai .................. | A61N 5/1042 378/65 |
| 7,433,503 | B2* | 10/2008 | Cherek ................ | A61B 5/0555 378/4 |
| 7,453,983 | B2* | 11/2008 | Schildkraut .......... | A61N 5/1049 378/205 |
| 7,505,559 | B2* | 3/2009 | Kuduvalli ............ | A61N 5/1049 378/205 |
| 7,590,218 | B2* | 9/2009 | Scherch ............... | A61N 5/1049 378/205 |
| 7,613,501 | B2* | 11/2009 | Scherch ............... | A61B 5/064 378/65 |
| 7,639,854 | B2* | 12/2009 | Schnarr ............... | A61N 5/103 382/128 |
| 7,640,607 | B2* | 1/2010 | Guertin ................. | A61B 5/064 5/601 |
| 7,657,301 | B2* | 2/2010 | Mate .................... | A61N 5/1049 128/899 |
| 7,715,606 | B2* | 5/2010 | Jeung .................. | A61B 90/36 378/65 |
| 7,720,196 | B2* | 5/2010 | Zhang ................. | A61B 5/113 378/65 |
| 7,729,472 | B2* | 6/2010 | Scherch ............... | A61B 6/0492 378/65 |
| 7,907,699 | B2* | 3/2011 | Long .................... | A61N 5/1049 378/65 |
| 7,945,021 | B2* | 5/2011 | Shapiro ................. | A61B 6/032 378/65 |
| 8,042,209 | B2* | 10/2011 | D'Souza ............. | A61N 5/1049 5/610 |
| 8,559,596 | B2* | 10/2013 | Thomson ............. | G06T 7/0014 378/65 |
| 8,747,382 | B2* | 6/2014 | D'Souza ............... | G16H 50/30 604/500 |
| 8,900,113 | B2* | 12/2014 | Raleigh ................ | A61N 5/1037 600/1 |
| 8,917,813 | B2* | 12/2014 | Maurer, Jr. .............. | A61N 5/10 378/65 |
| 8,948,842 | B2* | 2/2015 | Raleigh ................ | A61B 6/466 600/411 |
| 9,153,034 | B2* | 10/2015 | Mostafavi .............. | A61B 6/52 |
| 9,192,781 | B2* | 11/2015 | Ichihashi ............... | A61B 6/542 |
| 9,211,423 | B2* | 12/2015 | Gross .................... | A61N 5/1049 |
| 9,248,312 | B2* | 2/2016 | Li ......................... | A61N 5/1049 |
| 9,271,692 | B2* | 3/2016 | Mostafavi ............. | A61B 6/032 |
| 9,283,404 | B2* | 3/2016 | Raleigh ................. | A61B 8/085 |
| 9,364,687 | B2* | 6/2016 | Raleigh ................. | A61N 5/1077 |
| 9,392,962 | B2* | 7/2016 | Mostafavi ............ | A61N 5/1067 |
| 9,451,928 | B2* | 9/2016 | Falco .................... | A61B 8/483 |
| 9,486,647 | B2* | 11/2016 | Bergfjord ............. | A61N 5/1048 |
| 9,511,243 | B2* | 12/2016 | Yan ....................... | A61B 6/03 |
| 9,561,387 | B2* | 2/2017 | Yan ....................... | G01S 17/48 |
| 9,717,461 | B2* | 8/2017 | Yu ........................ | A61B 5/721 |
| 9,734,589 | B2* | 8/2017 | Yu ........................ | G06T 7/292 |
| 9,886,534 | B2* | 2/2018 | Wan ..................... | A61N 5/1048 |
| 9,913,996 | B2* | 3/2018 | Takahashi ........... | A61N 5/1049 |
| 9,939,130 | B2* | 4/2018 | Jeung ................... | A61B 5/1113 |
| 9,950,194 | B2* | 4/2018 | Bouchet ............... | A61N 5/1048 |
| 9,962,561 | B2* | 5/2018 | Meir ...................... | A61B 6/584 |
| 9,990,711 | B2* | 6/2018 | Lugosi .................. | G06T 7/0012 |
| 9,993,663 | B2* | 6/2018 | Sabczynski .......... | A61N 5/1037 |
| 10,035,026 | B2* | 7/2018 | Tijs ....................... | A61N 5/1049 |
| 10,065,049 | B2* | 9/2018 | Lugosi .................. | A61N 5/1049 |
| 10,080,910 | B2* | 9/2018 | Bharat ................. | A61N 5/1037 |
| 10,272,265 | B2* | 4/2019 | Filiberti ................. | A61N 5/1049 |
| 10,342,996 | B2* | 7/2019 | Jordan ................... | A61N 5/107 |
| 10,376,714 | B2* | 8/2019 | Bharat ................. | A61N 5/107 |
| 10,426,975 | B2* | 10/2019 | Bharat ................. | A61B 8/485 |
| 10,429,826 | B2* | 10/2019 | Ju ......................... | A61N 5/1075 |
| 10,500,418 | B2* | 12/2019 | Filiberti ................ | A61B 5/113 |
| 10,650,585 | B2* | 5/2020 | Kiely .................... | A61B 17/6235 |
| 10,737,118 | B2* | 8/2020 | Mostafavi .............. | A61B 6/032 |
| 10,821,301 | B2* | 11/2020 | Nishio .................. | A61N 5/1049 |
| 10,926,106 | B2* | 2/2021 | Berlinger ............... | A61B 6/032 |
| 10,952,695 | B2* | 3/2021 | Mori ...................... | G06T 7/246 |
| 10,981,019 | B2* | 4/2021 | Cordero Marcos .. | A61N 5/1038 |
| 11,024,084 | B2* | 6/2021 | Friman ................. | G06T 19/006 |
| 2002/0193685 | A1 | 12/2002 | Mate et al. | |

FOREIGN PATENT DOCUMENTS

| | | |
|---|---|---|
| JP | 2005-514969 | 5/2005 |
| JP | 2008-022896 | 2/2008 |
| JP | 2010-57549 | 3/2010 |
| JP | 2011-200542 | 10/2011 |
| JP | 2015-019693 | 2/2015 |
| JP | 2017-093516 | 6/2017 |
| WO | WO 2009/150708 A1 | 12/2009 |
| WO | WO 2017/101990 A1 | 6/2017 |

* cited by examiner

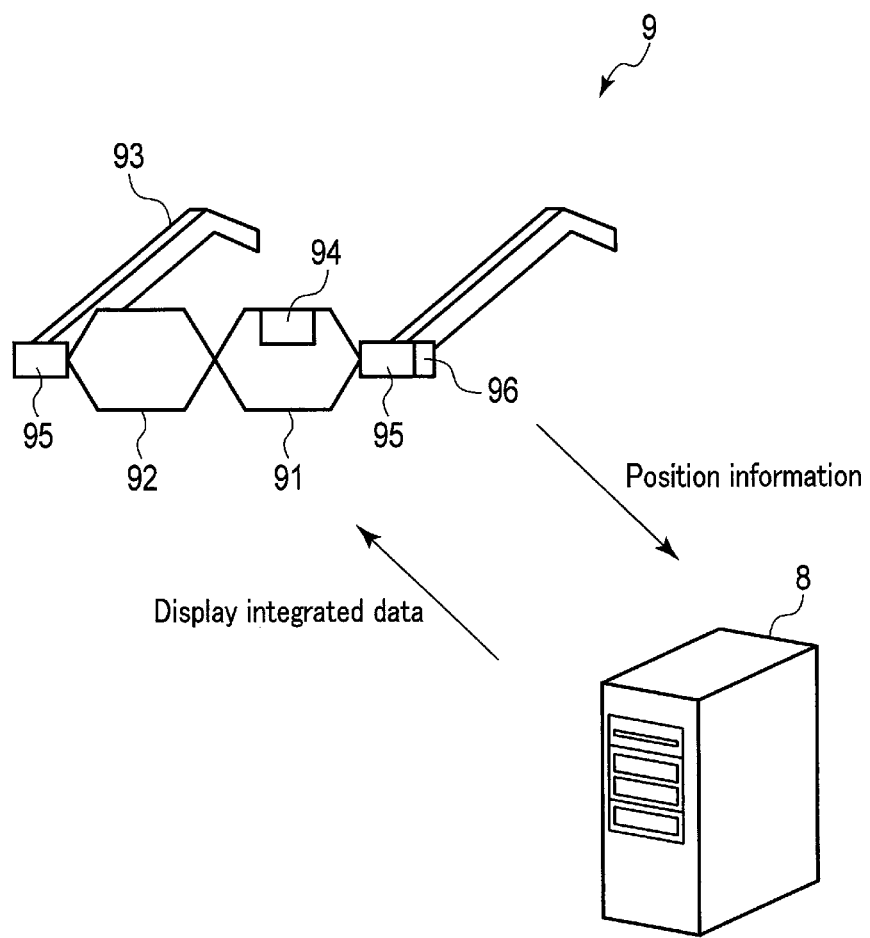
F I G. 18

RADIOTHERAPY SYSTEM AND TREATMENT SUPPORT APPARATUS

CROSS-REFERENCE TO RELATED APPLICATIONS

This application is based upon and claims the benefit of priority from the Japanese Patent Application No. 2017-127807, filed Jun. 29, 2017 and the Japanese Patent Application No. 2018-120610, filed Jun. 26, 2018, the entire contents of all of which are incorporated herein by reference.

FIELD

Embodiments described herein relate generally to a radiotherapy system and a treatment support apparatus.

BACKGROUND

At the time of radiotherapy, in order to irradiate the tumor position accurately, it is necessary to align the tumor roughly to the isocenter (hereinafter referred to as a first alignment). The first alignment is performed such that a mark indicating the tumor position is drawn on the front or the side of the body surface of a patient while referring to a planning CT image, and alignment of the patient, the bed, etc. is manually performed so that the mark matches with the irradiation position of the laser from the laser sighting instrument. This work is troublesome and inaccurate. In addition, since radiotherapy is performed over several days, the mark may disappear if the patient takes a bath or the like. If the mark disappears, it has to be drawn again. This work is also troublesome and inaccurate.

BRIEF DESCRIPTION OF THE DRAWING

FIG. 18 is a diagram showing the configuration of an information display system according to an application example.

DETAILED DESCRIPTION

In general, according to one embodiment, the radiotherapy system includes a medical image collecting device, a first body surface data collecting device and processing circuitry. The medical image collecting device collects medical three-dimensional image data of the patient at the time of treatment planning. The first body surface data collecting device collects first body surface data representing a three-dimensional body surface of the patient at the time of treatment planning. The processing circuitry may generate integrated data in which at least one of the medical three-dimensional image data and the treatment target region data included in the medical three-dimensional image data, and the first body surface data are integrated into an identical three-dimensional coordinate system.

First Embodiment

Figure 1:
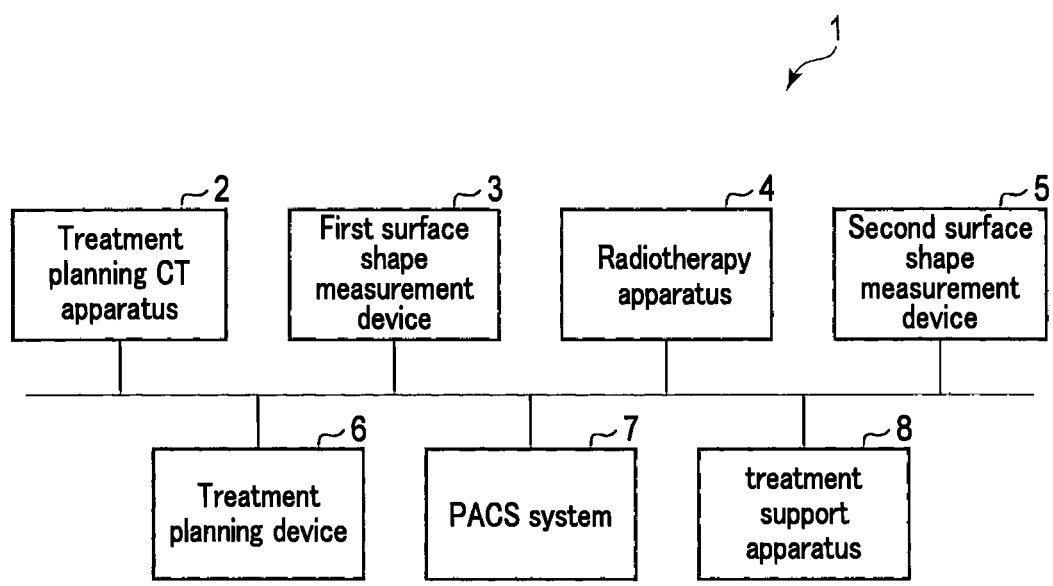
FIG. 1 is a diagram showing a configuration of a radiotherapy system according to a first embodiment.

FIG. 1 is a diagram showing a configuration of a radiotherapy system 1 according to a first embodiment. As shown in FIG. 1, the radiotherapy system 1 includes a treatment planning computed tomography (CT) apparatus 2, a first surface shape measurement device 3, a radiotherapy apparatus 4, a second surface shape measurement device 5, a treatment planning device 6, a picture archiving and communication system (PACS) system 7, and a treatment support apparatus 8. A treatment planning CT apparatus 2, the first surface shape measurement device 3, the radiotherapy apparatus 4, the second surface shape measurement device 5, the treatment planning device 6, the PACS system 7, and the treatment support apparatus 8 are communicably connected to each other.

Figure 2:
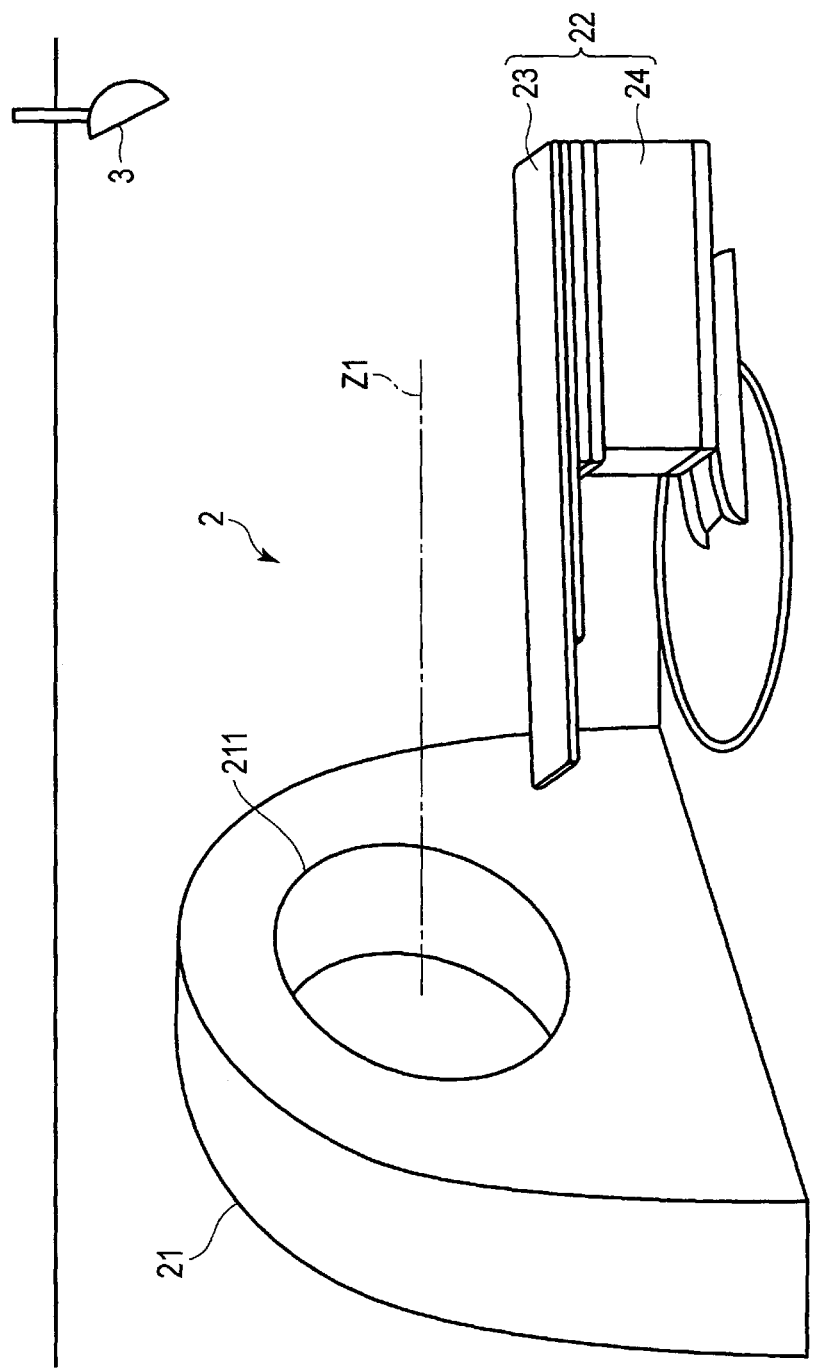
FIG. 2 is a diagram showing an installation environment between a treatment planning CT apparatus and a first surface shape measurement device in FIG. 1.

FIG. 2 is a diagram showing an installation environment between the treatment planning CT apparatus 2 and the first surface shape measurement device 3. As shown in FIG. 2, the treatment planning CT apparatus 2 and the first surface shape measurement device 3 are installed in a planning CT room. The treatment planning CT apparatus 2 includes an imaging gantry 21 and an imaging bed 22. Further, the treatment planning CT apparatus 2 includes a console (not shown) installed in an operation room adjacent to the planning CT room. The imaging gantry 21 has an opening 211 into which the patient is inserted, and a support mechanism (not shown) for rotatably supporting an X-ray tube (not shown) and an X-ray detector (not shown) around the rotation axis Z1 is mounted inside the imaging gantry 21. The imaging bed 22 includes an imaging top plate 23 on which the patient is placed and a base 24 for movably supporting the imaging top plate 23. The imaging top plate 23 has a planar shape similarly to a treatment top plate 44 described later. In order to improve the positioning accuracy of the patient, the imaging top plate 23 may have 20 the same shape as the treatment top plate 44.

At the time of CT imaging, the imaging gantry 21 performs X-ray irradiation by the X-ray tube and X-ray detection by the X-ray detector while rotating the X-ray tube and the X-ray detector at high speed, so that raw data showing attenuation of X-rays by the patient is collected by the X-ray detector. The raw data is transmitted to a console (not shown). The console reconstructs three-dimensional CT image data based on the raw data. The console may generate image data indicating the spatial distribution of a CT value according to the X-ray attenuation coefficient as the CT image data, and calculate the X-ray attenuation coefficient from the CT value to generate image data showing the spatial distribution of the X-ray attenuation coefficient may be generated. The CT image data is transmitted to the treatment planning device 6, the PACS system 7, and the treatment support apparatus 8.

Note that although the radiotherapy system 1 includes the treatment planning CT apparatus 2, the present embodiment is not limited to this. That is, as long as the radiotherapy system 1 is a medical image diagnostic apparatus capable of generating three-dimensional medical image data for a treatment plan of the patient, the radiotherapy system 1 may include a cone beam CT apparatus, a magnetic resonance imaging apparatus, and a nuclear medicine diagnostic apparatus, or the like instead of the treatment planning CT apparatus 2. However, in order to make the following description specifically, the radiotherapy system 1 includes a treatment planning CT apparatus 2 as a medical image diagnostic apparatus capable of generating three-dimensional medical image data for a treatment plan of the patient.

The first surface shape measurement device 3 is provided on the wall surface of the planning CT room. For example, the first surface shape measurement device 3 is suspended from the ceiling. The first surface shape measurement device 3 measures the body surface of the patient placed on the imaging top plate 23 and collects three-dimensional patient body surface data on the body surface of the patient.

Figure 3:
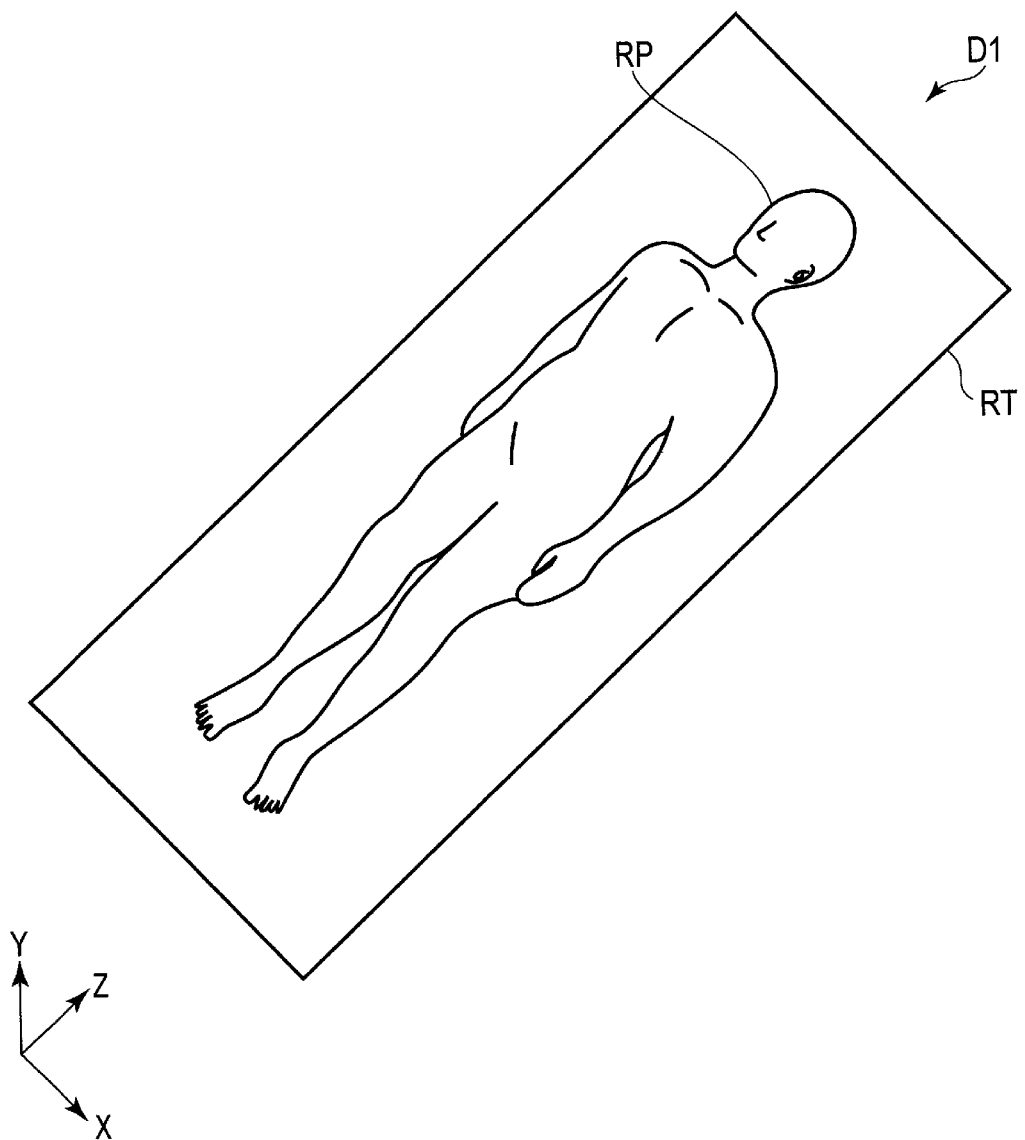
FIG. 3 is a diagram showing an example of three-dimensional patient body surface data collected by the first surface shape measurement device in FIG. 2.

FIG. 3 is a diagram showing an example of three-dimensional patient body surface data D1 collected by the first surface shape measurement device 3. As shown in FIG. 3, the patient body surface data D1 has a patient body surface area RP relating to the body surface of the patient P and a top plate surface area RT relating to the surface of the imaging top plate 23. The patient body surface data D1 is data that records a shape, a position, a size, etc. of the body surface of the patient measured according to a predetermined measurement principle. The patient body surface data D1 is defined by an XYZ orthogonal coordinate system. The Y axis is defined as a vertical axis, the Z axis is defined as the central axis R1 of the imaging gantry 21, and the X axis is defined as an axis orthogonal to the Y axis and the Z axis. Hereinafter, the three-dimensional body surface data on the body surface of the patient placed on the imaging top plate of the treatment planning CT apparatus 2 where the data is collected by the first surface shape measurement device 3 is referred to as planning-time body surface data. The planning-time body surface data is transmitted to the treatment support apparatus 8. Note that although the planning-time body surface data shown in FIG. 3 includes the patient body surface area RP relating to the whole body of the patient, it may contain only the patient body surface area RP related to the partial body surface of the patient. That is, the first surface shape measurement device 3 may optically scan only the partial body surface of the patient.

There are several measurement principles of the first surface shape measurement device 3. For example, a measurement principle includes an optical scanning method. In this case, the first surface shape measurement device 3 includes a light projecting unit, an imaging unit, and a three-dimensional coordinate identifying unit. The light projecting unit scans the patient placed on the imaging top plate 23 in a line shape with a laser. The imaging unit captures as an image the laser light on and around the patient in synchronization with the laser light projection. The three-dimensional coordinate identifying unit calculates the three-dimensional coordinates from the position of the laser projected light source of the light projecting unit and the laser position on the image, and the like. By this operation, one cross section of the patient's surface shape is obtained. By repeating the identification while changing the projection angle of the laser, it is possible to three-dimensionally obtain the shape of the patient's surface.

Another measurement principle includes an epipolar geometry method. In this case, the first surface shape measurement device 3 includes an image collecting section and an image processing section. The image collecting section includes two cameras. The image collecting section photographs the patient placed on the imaging top plate 23 with two cameras having different observation angles and collects two image data having different observation angles. The image processing section includes a processor and a memory. The image processing section sets one pixel (a focused point) of the image data relating to the first observation angle and identifies a corresponding point in the image data relating to the second observation angle corresponding to the focused point. Note that the focused point may be a small region including the pixel as its center. As the identification method, correlation calculation is generally used. When the corresponding point is identified, the image processing section Identify, based on the principle of epipolar geometry, the three-dimensional coordinates of the intersection of an imaging track (ray) connecting the point of interest included in the first image data and the first camera that has collected the first image data, and an imaging track connecting the corresponding point included in the second image data and the second camera which collected the second image data, The image processing section identifies the three-dimensional coordinates of the intersection for all pixels and identifies a set of intersections as the three-dimensional patient body surface data of the patient.

Although the two embodiments have been described as the measurement principle, the measurement principle of the first surface shape measurement device 3 according to the present embodiment is not limited thereto, and any method may be used as long as the body surface of the patient can be measured. In order to specifically describe below, the measurement principle of the first surface shape measurement device 3 is the optical scanning method.

Figure 4:
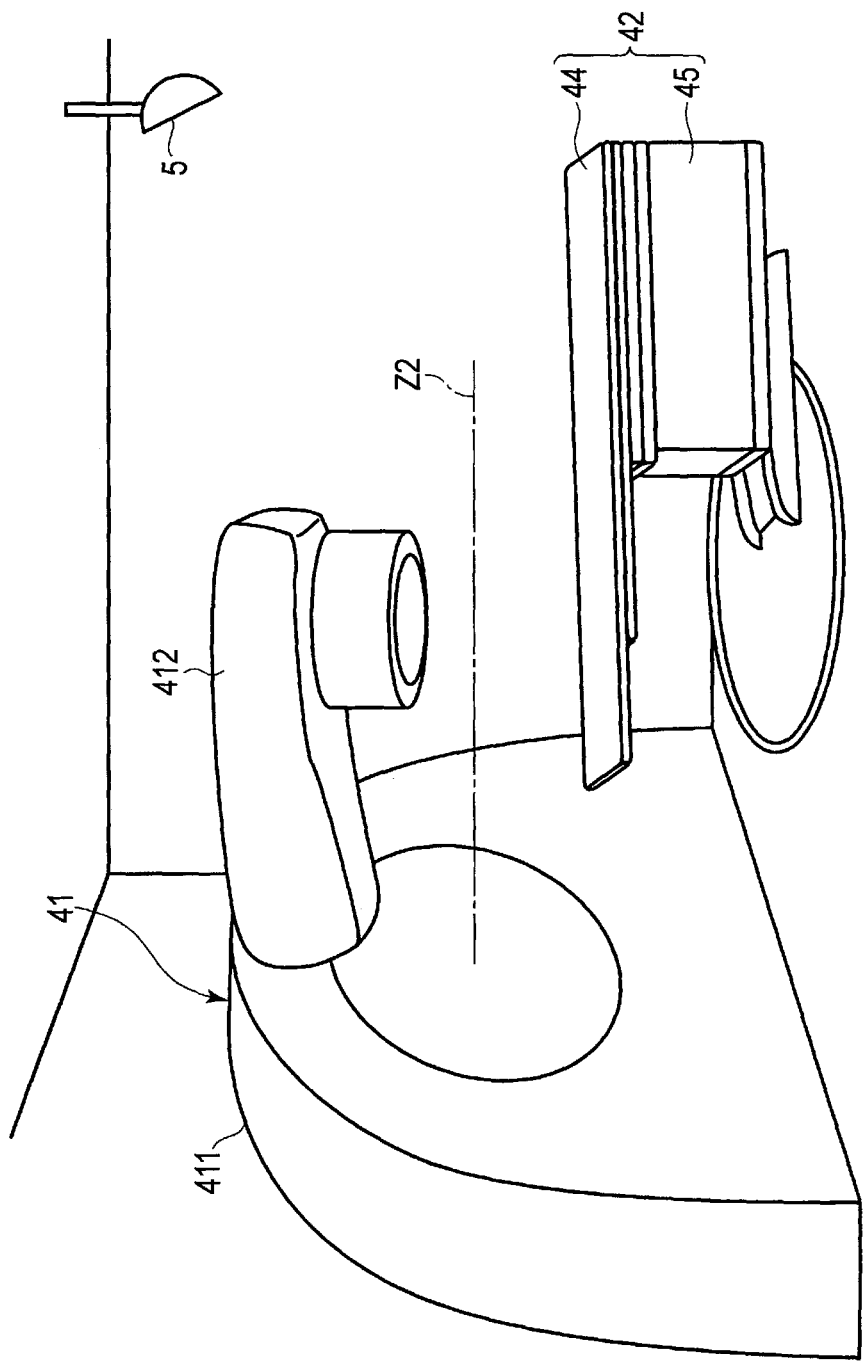
FIG. 4 is a diagram showing an installation environment between the radiotherapy apparatus in FIG. 1 and a second surface shape measurement device.

FIG. 4 is a diagram showing an installation environment between the radiotherapy apparatus 4 and the second surface shape measurement device 5. As shown in FIG. 4, the radiotherapy apparatus 4 and the second surface shape measurement device 5 are installed in a treatment room. The radiotherapy apparatus 4 includes a treatment gantry 41 and a treatment bed 42. Further, the radiotherapy apparatus 4 includes a console (not shown) installed in the operation room adjacent to the treatment room. The treatment gantry 41 includes a gantry main body 411 installed on the wall surface of the treatment room. The gantry main body 411 rotatably supports an irradiation head unit 412 around a rotation axis Z2. The treatment bed 42 includes the treatment top plate 44 on which the patient is placed and a base 45 that movably supports the treatment top plate 44. The treatment top plate 44 has a planar shape similarly to the imaging top plate 23.

The second surface shape measurement device 5 is provided on the wall surface of the treatment room. For example, the second surface shape measurement device 5 is suspended from the ceiling. The second surface shape measurement device 5 measures the body surface of the patient placed on the treatment top plate 44 and collects three-dimensional patient body surface data on the body surface of the patient. Hereinafter, three-dimensional patient body surface data on the body surface of the patient placed on the treatment top plate of the radiotherapy apparatus 4 where the data is collected by the second surface shape measurement device 5 will be referred to as treatment-time body surface data. The second surface shape measurement device 5 collects treatment-time body surface data according to the same principle as that of the first surface shape measurement device 3. The treatment-time body surface data is transmitted to the treatment support apparatus 8.

Figure 5:
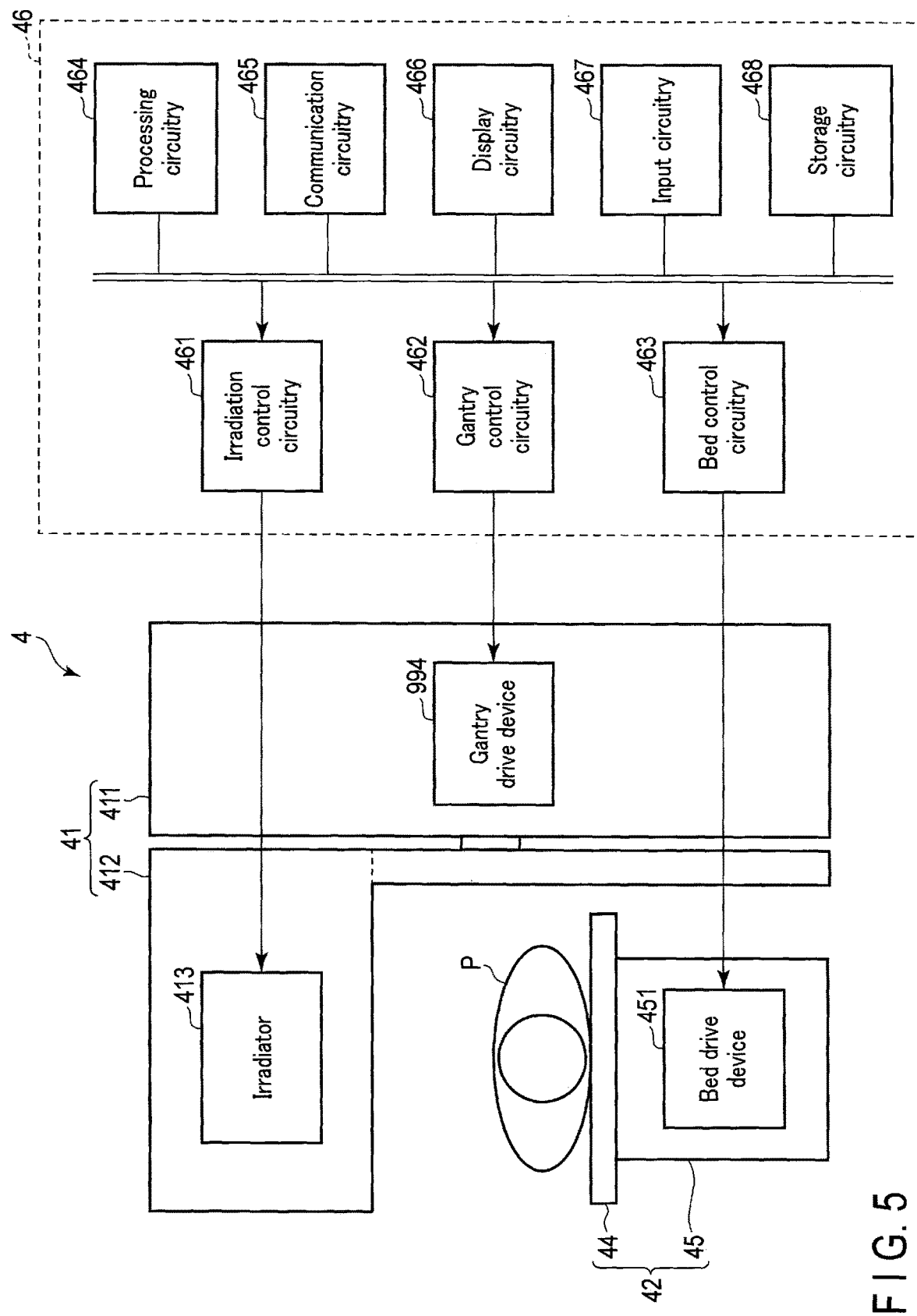
FIG. 5 shows a configuration of the radiotherapy apparatus in FIG. 3.

FIG. 5 shows the arrangement of the radiotherapy apparatus 4. As shown in FIG. 5, the radiotherapy apparatus 4 includes a treatment gantry 41, the treatment bed 42, and a console 46.

The treatment gantry 41 includes the gantry main body 411 and the irradiation head unit 412. The gantry main body 411 is installed on the floor surface and rotatably supports the irradiation head unit 412 around the rotation axis Z2. The irradiation head unit 412 is attached to the gantry main body 411. An irradiator 413 is incorporated in the irradiation head unit 412. The irradiator 413 includes an acceleration tube (not shown) for accelerating electrons or the like generated by an electron gun or the like, and a metal target (not shown) with which electrons accelerated by the acceleration tube collide. When electrons collide with the metal target, X-rays as radiation are generated. The irradiator 413 receives a control signal from irradiation control circuitry 461 of the console 46 and emits the radiation. The point where the beam axis of the irradiation head unit 412 and the rotation axis Z2 intersect is spatially immobile and is called an isocenter.

The irradiation head unit 412 is provided with a multi-leaf collimator (MLC: Multi Leaf Collimator) (not shown). The multi-leaf collimator movably supports a plurality of leaves formed by the X-ray shielding material. By moving a plurality of leaves, it is possible to form an irradiation field with any shape.

A gantry drive device 994 is built in the gantry main body 411. The gantry drive device 994 receives the control signal from gantry control circuitry 462 of the console 46 and rotates the irradiation head unit 412 around the rotation axis Z2.

A bed drive device 451 is incorporated in the treatment bed 42. The bed drive device 451 receives the control signal from bed control circuitry 463 of the console 46 and moves the treatment top plate 44.

As shown in FIG. 5, the console 46 includes the irradiation control circuitry 461, the gantry control circuitry 462, the bed control circuitry 463, processing circuitry 464, communication circuitry 465, display circuitry 466, input circuitry 467, and storage circuitry 468.

The irradiation control circuitry 461 controls the irradiator 413 in order to emit the radiation according to the irradiation condition based on the treatment plan transmitted from the treatment planning device 6. It should be noted that the irradiation conditions may be input by a user such as a radiotherapy practician via the input circuitry 467. The irradiation control circuitry 461 includes a processor such as a central processing unit (CPU) and a memory such as a read only memory (ROM) and a random access memory (RAM) as a hardware resource.

The gantry control circuitry 462 controls the gantry drive device 994 in order to emit the radiation from the irradiation angle based on the treatment plan transmitted from the treatment planning device 6. The irradiation angle may be input by the user via the input circuitry 467. The gantry control circuitry 462 includes a processor such as a CPU and a memory such as a ROM and a RAM as a hardware resource.

The bed control circuitry 463 transmits a control signal to the bed drive device 451 in order to move the treatment top plate 44 to any positions. The position of the treatment top plate 44 may be input by the user via the input circuitry 467. In addition, the bed control circuitry 463 controls the bed drive device 451 in order to match the position of the treatment body part of the patient to the isocenter. The bed control circuitry 463 includes a processor such as a CPU and a memory such as a ROM and a RAM as a hardware resource.

The processing circuitry 464 functions as the main unit of the radiotherapy apparatus 4. The processing circuitry 464 executes the operation program according to the present embodiment stored in the storage circuitry 468 or the like and performs the radiotherapy according to the present embodiment by controlling each unit according to the operation program. The processing circuitry 464 includes a processor such as a CPU and a memory such as a ROM and a RAM as a hardware resource.

The communication circuitry 465 performs data communication with the treatment planning device 6, the PACS system 7, and the treatment support apparatus 8 that constitute the radiotherapy system 1 via wired or wireless (not shown).

The display circuitry 466 displays various information. More specifically, the display circuitry 466 includes a display interface and a display device. The display interface converts data representing a display target into a video signal. The video signal is supplied to the display device. The display device displays the video signal representing the display target. As a display device, it is possible to use, for example, a CRT display, liquid crystal display, organic EL display, LED display, plasma display, or arbitrary display known in this technical field. The display device may be provided on the gantry main body 411 or may be provided on the wall surface of the treatment room. In addition, the display device may be a projector.

More specifically, the input circuitry 467 includes an input device and an input interface. The input device accepts various types of commands from the user. As input devices, it is possible to use a keyboard, mouse, various types of switches, and the like. The input interface supplies output signals from the input device to the processing circuitry 464 via a bus.

The storage circuitry 468 is a storage device such as a hard disk drive (HDD), a solid state drive (SSD), or an integrated circuitry storage device, which store various types of information. For example, the storage circuitry 468 stores a radiotherapy plan and the like. As the hardware, the storage circuitry 468 may be a drive assembly or the like which reads and writes various types of information from and to portable storage media such as a CD-ROM drive, DVD drive, and flash memory.

As shown in FIG. 1, the treatment planning device 6 is a computer for planning a treatment plan based on the CT image transmitted from the treatment planning CT apparatus 2. The radiotherapy plan prepared in this manner is sent to the radiotherapy apparatus 4 and the treatment support apparatus 8.

The PACS system 7 includes an image server that manages medical image data such as CT image data generated by the treatment planning CT apparatus 2.

Figure 6:
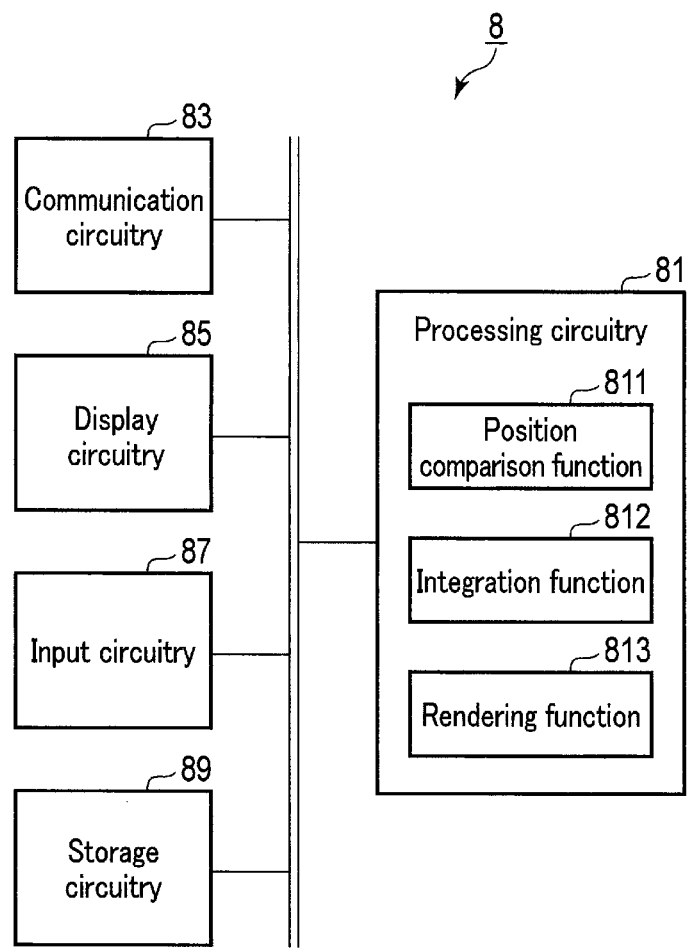
FIG. 6 is a diagram showing the configuration of the treatment support apparatus in FIG. 1.

The treatment support apparatus 8 is a computer for supporting radiotherapy by the radiotherapy apparatus 4. FIG. 6 is a diagram showing the configuration of the treatment support apparatus 8 according to the first embodiment. As shown in FIG. 6, the treatment support apparatus 8 includes processing circuitry 81, communication circuitry 83, display circuitry 85, input circuitry 87, and storage circuitry 89. The processing circuitry 81, the communication circuitry 83, the display circuitry 85, the input circuitry 87, and the storage circuitry 89 are communicably connected to each other via a bus.

The processing circuitry 81 includes, as hardware resources, a processor such as a CPU, a graphics processing unit (GPU), and a memory such as a ROM and a RAM. The processing circuitry 81 executes a program relating to a radiotherapy support (hereinafter referred to as a radiotherapy support program) and performs radiotherapy support by the radiotherapy apparatus 4. The processing circuitry 81 according to the first embodiment performs a position comparison function 811, an integration function 812, and a rendering function 813 at the time of radiotherapy support.

In the position comparison function 811, the processing circuitry 81 compares a position of the planning-time body surface data collected by the first surface shape measurement device 3 with a position of the treatment-time body surface data collected by the second surface shape measurement device 5.

In the integration function 812, the processing circuitry 81 generates integrated data of at least one of the planning-time body surface data collected by the first surface shape measurement device 3 and the treatment target region data included in the CT image data and the CT image data. The integrated data is used to position the patient in radiotherapy.

In the rendering function 813, the processing circuitry 81 executes, on three-dimensional CT image data, planning-time integrated data, planning-time body surface data, and treatment-time body surface data, three-dimensional image processing such as volume rendering, surface volume rendering, pixel value projection processing, multi-planer reconstruction (MPR) processing, curved MPR (CPR) processing, etc., thereby generating a two-dimensional image for display.

The communication circuitry 83 performs, via wired or wireless (not shown), data communication between the treatment planning CT apparatus 2, the first surface shape measurement device 3, the radiotherapy apparatus 4, the second surface shape measurement device 5, the treatment planning device 6 and the PACS system 7 constituting the radiotherapy system 1.

The display circuitry 85 displays various information. More specifically, the display circuitry 85 includes a display interface and a display device. The display interface converts data representing a display target into a video signal. The video image is supplied to the display device. The display device displays the video signal representing the display target. As a display device, it is possible to use, for example, a CRT display, liquid crystal display, organic EL display, LED display, plasma display, or arbitrary display known in this technical field.

More specifically, the input circuitry 87 includes an input device and an input interface. The input device accepts various types of commands from the user. As input devices, it is possible to use a keyboard, mouse, various types of switches, and the like. The input interface supplies output signals from the input device to the processing circuitry 81 via a bus.

The storage circuitry 89 is a storage device such as a hard disk drive (HDD), a solid state drive (SSD), or an integrated circuitry storage device, which store various types of information. Alternatively, the storage circuitry 89 may be a drive assembly or the like which reads and writes various types of information from and to portable storage media such as a CD-ROM drive, DVD drive, and flash memory.

Note that the radiotherapy system 1 includes one treatment support apparatus 8. However, this embodiment is not limited to this. For example, the treatment support apparatus 8 may be provided in each of the operation room adjacent to the planning CT room and the operation room adjacent to the treatment room. Note that in the following description, the radiotherapy system 1 includes one treatment support apparatus 8 provided in the operation room adjacent to the treatment room.

Figure 7:
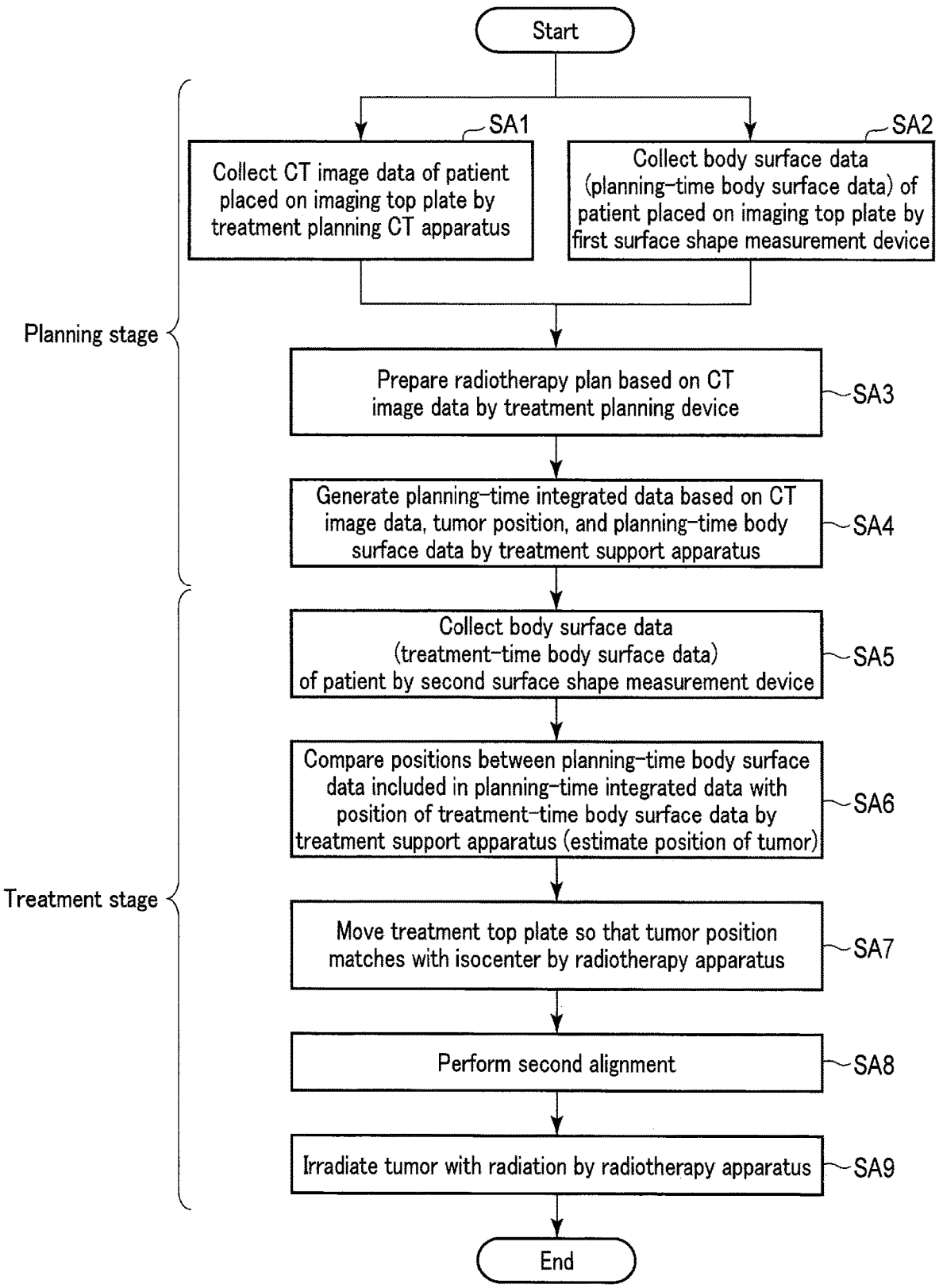
FIG. 7 is a diagram showing a typical flow of the operation of the radiotherapy system in FIG. 1.

Next, an operation example of the radiotherapy system 1 according to the first embodiment will be described. FIG. 7 is a diagram showing a typical flow of the operation of the radiotherapy system 1 according to the first embodiment. As shown in FIG. 7, the operation of the radiotherapy system 1 is divided into a planning stage and a treatment stage. The process in the planning stage is steps SA1 to SA4, and the process in the treatment stage is steps SA5 to SA8. The planning stage is a stage to formulate a radiotherapy plan for the patient to be treated prior to radiotherapy. The treatment stage is a stage of performing radiotherapy according to the radiotherapy plan. The planning stage and the treatment stage are typically performed on different days. Radiotherapy is usually performed over several days. The process in the treatment stage is repeated for each day when radiotherapy is performed.

In the planning stage, first, step SA1 by the treatment planning CT apparatus 2 and step SA2 by the first surface shape measurement device 3 are performed in parallel or in sequence. In step SA1, the treatment planning CT apparatus 2 performs CT imaging on the patient placed on the imaging top plate 23 and collects CT image data of the patient. In step SA2, the first surface shape measurement device 3 collects the planning-time body surface data of the patient placed on the imaging top plate 23 of the treatment planning CT apparatus 2.

Detailed process of steps SA1 and SA2 will be described. First, the radiotherapy practician guides the patient who entered the planning CT room on the imaging top plate 23 of the treatment planning. CT apparatus 2, and places the fixing tool to the patient in the same manner as in the time of radiotherapy. For example, the fixing tool may be installed between the patient and the imaging top plate 23, and shaped according to the physical structure of the patient, or may cover the patient's surface from above to prevent movement of the patient. Especially, the fixing tool for the head part is formed of a mesh-like member, and it is formed so as to be breathable even in a state of covering the patient's head.

In the case where the imaging top plate 23 is disposed at the initial position, the first surface shape measurement device 3 optically scans the patient placed on the imaging top plate 23 to collect the three-dimensional planning-time body surface data. The initial position is a position of the imaging top plate 23 before the movement for inserting the imaging top plate 23 into the opening 211 of the imaging gantry 21 is started. The collected planning-time body surface data is transmitted to the treatment support apparatus 8. Next, a planning CT apparatus 2 inserts the imaging top plate 23 on which the patient is placed into the opening 211 of the imaging gantry 21, and performs CT imaging to collect CT image data. The CT image data is transmitted from the treatment planning CT apparatus 2 to the treatment planning device 6 and the PACS system 7.

After completing the CT imaging, the planning CT apparatus 2 returns the imaging top plate 23 to the initial position. The first surface shape measurement device 3 optically scans the patient placed on the imaging top plate 23 arranged at the initial position again to collect three-dimensional planning-time body surface data. The collected planning-time body surface data is transmitted to the treatment support apparatus 8.

The processing circuitry 81 of the treatment support apparatus 8 performs the position comparison function 811. In the position comparison function 811, the processing circuitry 81 calculates the amount of positional deviation between the body surface area of the initial planning-time body surface data and the body surface area of the final planning-time body surface data, and determines whether the positional deviation amount is within a predetermined allowable range. When it is determined that the positional deviation amount is within the allowable range, either one of the first planning-time body surface data and the last planning-time body surface data is selected as the planning-time body surface data to be used for future processing. When it is out of the allowable range, the processing circuitry 81 calculates the amount of positional deviation between the patient body surface area identified from the CT image data and the patient body surface area of the initial planning-time body surface data, and calculates the amount of positional deviation between the patient body surface area included in the CT image data and the patient body surface area of the last planning-time body surface data, and selects the planning-time body surface data with a smaller amount of positional deviation as the planning-time body surface data to be used for future processing.

When steps SA1 and SA2 are performed, the treatment planning device 6 prepares a radiotherapy plan based on the CT image data collected in step SA1 (step SA3).

Specifically, in step SA3, the treatment planning device 6 receives the CT image data directly from the treatment planning CT apparatus 2 or via the PACS system 7. The treatment planning device 6 prepares a radiotherapy plan based on the CT image data.

There are two kinds of methods, that is, Forward Planning and Inverse Planning, for preparing a radiotherapy plan. For Forward Planning, the radiotherapy conditions such as the number of irradiation directions of radiotherapy, each irradiation angle, the radiation intensity of each irradiation, the collimator opening degree of each irradiation, the wedge filter and the like are set in detail, and by looking at the finally obtained radiation distribution with such conditions, radiotherapy conditions are determined. When changing the radiation distribution, part or all of the radiotherapy condition are changed, and the radiation distribution is obtained again. As described above, in Forward Planning, the radiation distribution is gradually changed while changing the radiotherapy condition, and the radiation conditions are repeatedly changed repeatedly until the desired radiation distribution can be obtained. For Inverse planning the tumor region and an appropriate margin are set and the radiation quantity to be applied to the area and its allowable range are set. Furthermore, a risk region such as a critical organ is extracted from the CT image data, and the radiation quantity for the risk region is set to a safety level not exceeding a predetermined level. The radiotherapy apparatus 4 sequentially prepares a radiotherapy plan that satisfies the requirement for this radiation distribution while changing the radiotherapy condition. The radiotherapy plan and the position of the tumor region are transmitted to the treatment support apparatus 8.

When step SA3 is performed, the processing circuitry 81 of the treatment support apparatus 8 performs the integration function 812 (step SA4). In step SA4, the processing circuitry 81 generates planning-time integrated data based on the CT image data, the tumor region data, and the planning-time body surface data.

It is necessary to register individual three-dimensional coordinate systems of the first surface shape measurement device 3 and the treatment planning CT apparatus 2 for integration. This is done using a dedicated calibration phantom. The calibration phantom has a plurality of markers with irregularities on its surface. The number of markers is 3 or more. As in the patient, the first surface shape measurement device 3 optically scans the calibration phantom to collect surface shape data on the calibration phantom. The treatment planning CT apparatus 2 CT images the relevant calibration phantom and collects CT image data. The surface shape data and the CT image data relating to the calibration phantom are transmitted from the treatment planning CT apparatus 2 to the treatment support apparatus 8.

The processing circuitry 81 of the treatment support apparatus 8 identifies markers for each of the surface shape data and the CT image data on the calibration phantom by image processing and calculates correction parameters for matching the three-dimensional coordinate systems of both markers. The processing circuitry 81 integrates the CT image data and the planning-time body surface data on the patient in the same three-dimensional coordinate system based on the correction parameter to generate integrated data. Further, the processing circuitry 81 extracts the tumor region from the CT image data on the patient and identifies the position in the CT image data of the extracted tumor region. The processing circuitry 81 attaches the mark indicating the position of the tumor region to the integrated data in a position-aligned manner based on the correction parameter. Hereinafter, the integrated data of the CT image data, the planning-time body surface data, and the tumor position on the patient will be referred to as planning-time integrated data. The planning-time integrated data is transferred to the radiotherapy apparatus 4 and other devices. Thus, the process in the planning stage is completed.

Figure 8:
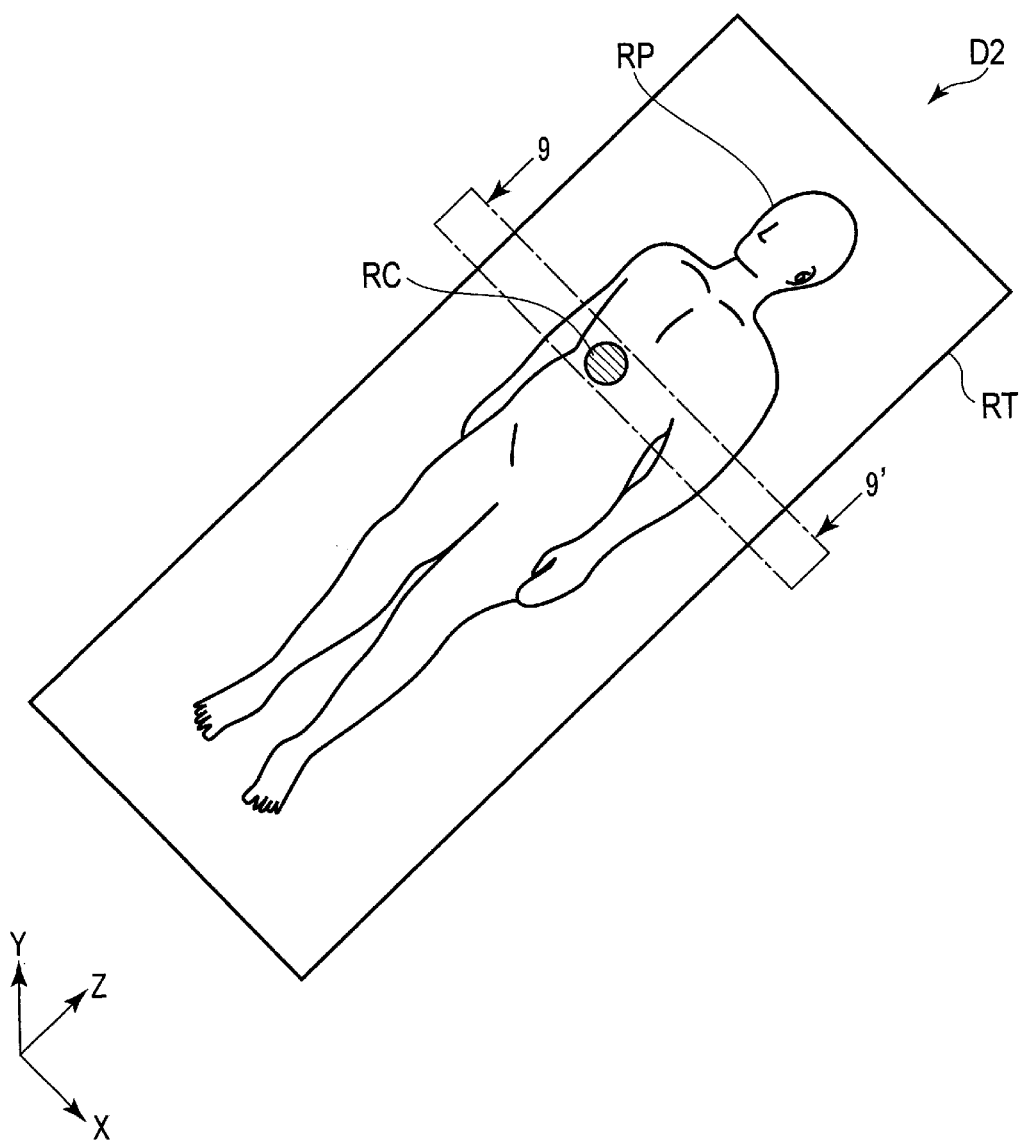
FIG. 8 is a diagram showing an example of planning-time integrated data generated in step SA4 in FIG. 7.
Figure 9:
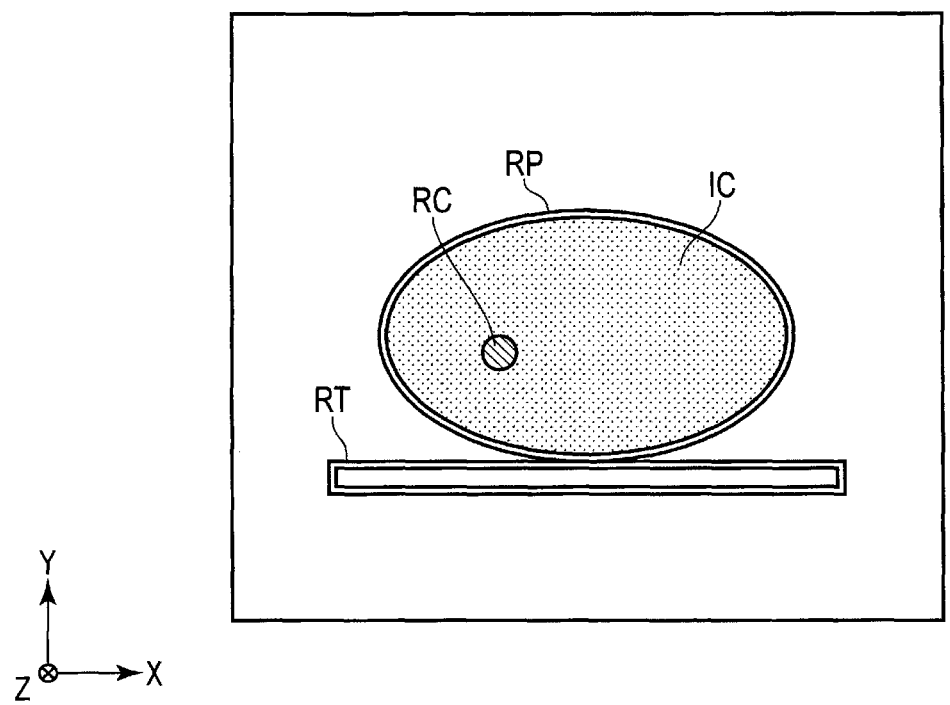
FIG. 9 is a cross-sectional view taken along line 9-9' in FIG. 8.

FIG. 8 is a diagram showing an example of planning-time integrated data D2 generated in step SA4. FIG. 9 is a cross-sectional view taken along line 9-9' in FIG. 8. As shown in FIGS. 8 and 9, the planning-time integrated data D2 has a patient body surface area RP and the top plate surface area RT derived from the planning-time body surface data, CT image data IC, and a tumor position RC. The tumor position RC is designated at the time of treatment planning using the CT image data IC.

As described above, planning-time integrated data is a data set that spatially integrates planning-time body surface data relating to the body surface of the patient, CT image data, and a tumor position at the time of CT imaging at the planning stage. The radiotherapy system 1 according to the present embodiment can easily and accurately adjust the tumor position at the time of treatment to the isocenter by using the planning-time integrated data. Therefore, marking of the tumor position with respect to the patient, which is conventionally necessary in the planning stage, is unnecessary in the present embodiment.

For example, planning-time integrated data is used in the treatment stage as follows. In the treatment stage, the second surface shape measurement device 5 collects treatment-time body surface data on the patient placed on the treatment top plate 44 of the radiotherapy apparatus 4 (step SA5). Specifically, first, the radiotherapy practician puts the patient who entered the treatment room on the treatment top plate 44, and places a fixing tool to the patient in the same manner as in the CT imaging in the planning stage. At the stage when the treatment top plate 44 is placed at the initial position, the second surface shape measurement device 5 optically scans the patient and collects three-dimensional treatment-time body surface data. The initial position is a position of the treatment top plate before the movement of the treatment top plate 44 to the isocenter of the treatment gantry 41 is started. Similarly to the planning-time body surface data, the treatment-time body surface data includes the patient body surface area related to the body surface of the patient placed on the treatment top plate 44 and the top plate surface area related to the surface of the treatment top plate 44. The treatment-time body surface data is transmitted to the treatment support apparatus 8. Note that from Step SA5 onward, the second surface shape measurement device 5 repeatedly optically scans the patient placed on the treatment top plate 44 to repeatedly collect the treatment-time body surface data.

When the step SA5 is performed, the processing circuitry 81 of the treatment support apparatus performs the position comparison function 811 (step SA6). In step SA6, the processing circuitry 81 compares positions between the planning-time body surface data included in the planning-time integrated data and the treatment-time body surface data collected by the second surface shape measurement device 5 to estimate the tumor position of the patient at the present time (treatment stage).

Specific examples of position comparison and tumor position estimation will be described below.

Figure 10:
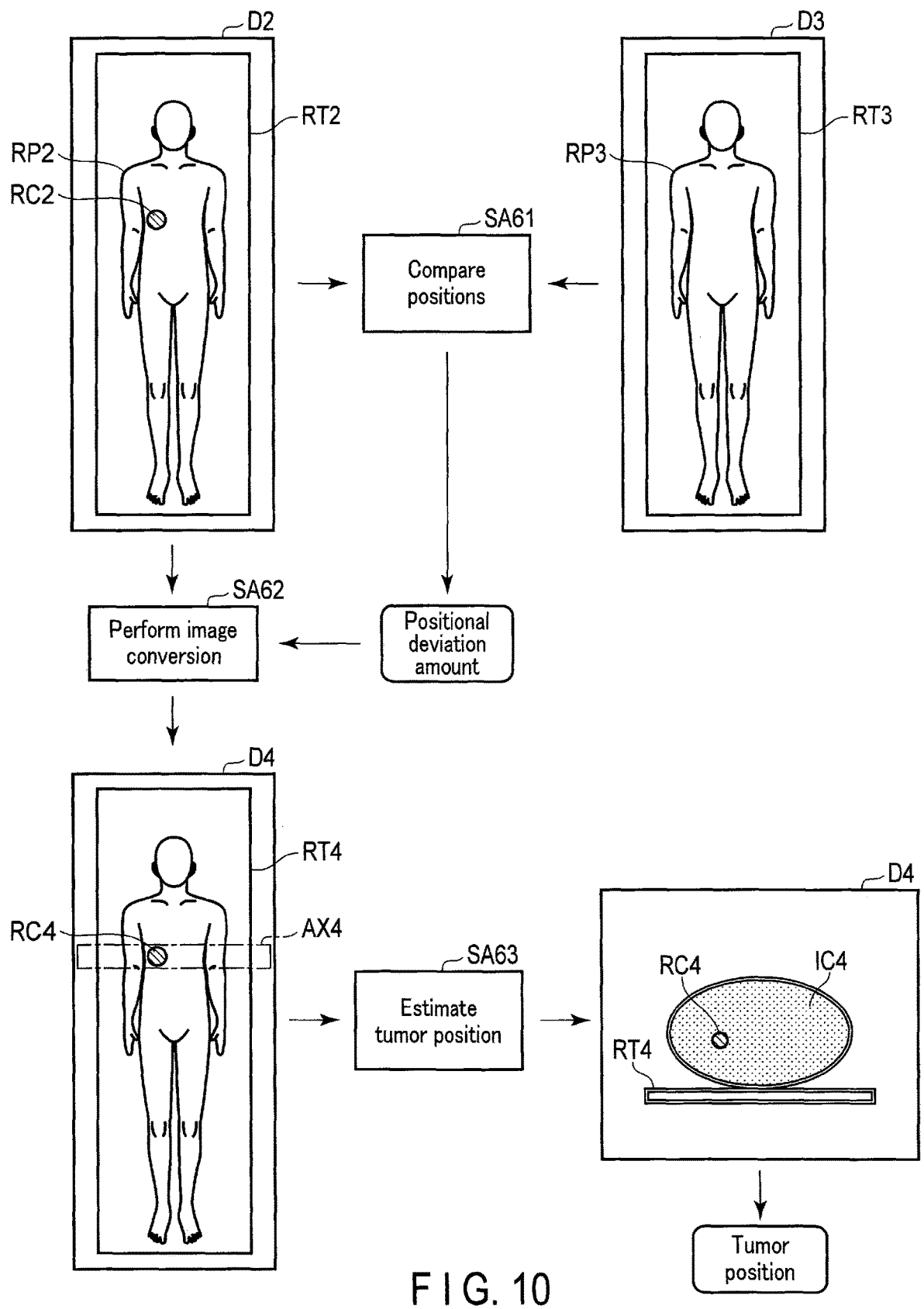
FIG. 10 is a diagram schematically showing the flow of a process of position comparison and tumor position estimation executed by processing circuitry of the treatment support apparatus in step SA6 in FIG. 7.

FIG. 10 is a diagram schematically showing the flow of a process of position comparison and tumor position estimation executed by processing circuitry 81 of the treatment support apparatus 8 in step SA6. Note that in FIG. 10, for the sake of clarity of description, patient body surface data D2, D3, and D4 are shown not three-dimensionally, but planarly. As shown in FIG. 10, first, the processing circuitry 81 reads the planning-time integrated data D2 and treatment-time body surface data D3. The planning-time integrated data D2 has at least a patient body surface area RP2 and a tumor position RC2. The treatment-time body surface data D3 has a patient body surface area RP3. No tumor position is shown to the patient body surface area RP3.

The processing circuitry 81 compares positions between the patient body surface area RP2 of the planning-time integrated data D2 and the patient body surface area RP3 of the treatment-time body surface data D3 and calculates the amount of positional deviation between the patient body surface area RP2 and the position of the patient body surface area RP3 (step SA61). The positional deviation amount is defined by the difference between the reference point of the patient body surface area RP2 and the corresponding point of the patient body surface area RP3. Typically, under the condition that the imaging top plate 23 or the treatment top plate 44 is located at the same height, the difference between the reference point of the patient body surface area RP2 and the corresponding point of the patient body surface area RP3 in the top plate surface of the imaging top plate 23 or the treatment top plate 44 is defined as the amount of positional deviation. The reference points and the corresponding points are set over a plurality of places. It should be noted that when compares positions between the patient body surface area RP2 of the planning-time integrated data D2 and the patient body surface area RP3 of the treatment-time body surface data D3, it may be undesirable to compare the entire area. For example, when treating a tumor of the liver, when the angle of the neck, shoulder, or hip joint is deviated between the time of planning CT imaging and the time of radiotherapy treatment, deviation for the idiosoma will occur by integrally matching these angles. In order to solve such a problem, the processing circuitry 81 roughly recognizes the head, torso, hands, and legs from each of the patient body surface area RP2 and the patient body surface area RP3, and compares positions using only the body part containing the tumor. In this way, by comparing positions of only the body part containing the tumor, no deviation for the idiosoma occurs, so that the accuracy of position comparison improves.

Next, as shown in FIG. 10, the processing circuitry 81 image-converts the planning-time integrated data D2 according to the positional deviation amount to match the position of the patient body surface area RP2 included in the planning-time integrated data D2 to the position of the patient body surface area RP3 included in the treatment-time body surface data D3 (step SA62). For image conversion, linear conversion such as movement, rotation, enlargement and reduction, or nonlinear conversion may be used. The image deformation by the position comparison function 811 is typically a linear conversion such as movement or rotation. That is, in the image deformation by the position comparison function 811, the shapes of the patient body surface area RP2 and the patient body surface area RP3 are not deformed.

Next, as shown in FIG. 10, the processing circuitry 81 estimates the tumor position of the patient at the present time (at the time of collecting the treatment-time body surface data) based on planning-time integrated data D4 after the image conversion (step SA63). Specifically, the processing circuitry 81 identifies a tumor position RC4 included in the planning-time integrated data D4. Then, the processing circuitry 81 specifies three-dimensional coordinates of the position of the tumor region RT 4 included in the CT image data IC4 of the axial cross section AX4. The identified position of the tumor region RC4 is presumed to be the tumor position of the patient at the time when the treatment-time body surface data was collected by the second surface shape measurement device 5. The three-dimensional coordinate data of the tumor position is transmitted to the radiotherapy apparatus 4.

When step SA6 is performed, the bed control circuitry 463 of the radiotherapy apparatus 4 moves the treatment top plate 44 so that the tumor position identified in step SA6 matches with the isocenter of the treatment gantry 41 (step SA7). The bed control circuitry 463 first determines the control parameters of the treatment bed 42 such that the tumor position matches with the isocenter of the treatment gantry. Specifically, the bed control circuitry 463 calculates the distance and direction to the three-dimensional coordinates of the isocenter of the treatment gantry 41 from the three-dimensional coordinates of the tumor position, and determines the control parameters corresponding to the calculated distance and direction, and supplies a driving signal according to the determined control parameter to the bed drive device 451. The bed drive device 451 receives the supplied driving signal and moves the treatment top plate 44. As a result, the tumor position identified in step SA6 matches with the isocenter of the treatment gantry 41. That is, it is possible to match the tumor position of the patient to the isocenter without manually adjusting the position of the patient placed on the treatment top plate 44. As described above, according to the present embodiment, by using the planning-time integrated data, it is possible to accurately and simply perform a first alignment of the patient without using a marker, a laser sighting instrument, or the like.

When the step SA7 is performed, the radiotherapy apparatus 4 carries out a second alignment (step SA8). The second alignment serves to complement the first alignment and is a finer alignment comparing with the first alignment. In the second alignment, the processing circuitry 464 of the radiotherapy apparatus 4 generates an X-ray image captured by the two-way X-ray image capturing system attached to the radiotherapy apparatus 4, for example, and a digitally reconstructed radiography (DRR) image projected as if the treatment planning CT image is captured in the two-way X-ray image capturing system. The processing circuitry 464 compares the tumor region and the anatomical feature point included in the DRR image with the corresponding points (the same tumor region and the anatomical feature point) included in the X-ray image and calculates the positional deviation amount.

Then, the bed control circuitry 463 moves the treatment top plate 44 according to the positional deviation amount. As a result, it is possible to precisely match the tumor region identified in the treatment planning CT image to the isocenter. Note that the patient himself may move or the patient may be moved by a radiotherapy practician so that the tumor region identified in the treatment planning CT image matches with the isocenter.

As another method of the second alignment, the processing circuitry 464 may compare the tumor region and the anatomical feature point included in the cone-beam CT image captured by the cone-beam CT imaging system attached to the radiotherapy apparatus 4 with the corresponding point (the same tumor region and anatomical feature point) included in the treatment planning CT image and calculate the positional deviation amount. The bed control circuitry 463 moves the treatment top plate 44 according to the positional deviation amount. As a result, it is possible to precisely match the tumor region identified in the treatment planning CT image to the isocenter. Even in this another method, the patient himself may move or the patient may be moved by the radiotherapy practician so that the tumor region identified in the treatment planning CT image matches with the isocenter. With the second alignment, accurate alignment is performed.

When the step SA8 is performed, the radiotherapy apparatus 4 irradiates the tumor of the patient with the radiation (step SA9). For example, in the case of planning to irradiate the tumor with X-rays from the patient front direction and the left side of the patient, gantry control circuitry 462 causes the irradiation head unit 412 to be arranged in front of the patient. Next, the irradiation control circuitry 461 adjusts the opening of the multi-leaf collimator in order to match the shape of the irradiation field of the X-ray to the shape of the tumor. Note that in addition to adjusting the aperture of the multi-leaf collimator, a wedge filter or the like for removing the low energy component of the X-ray may be inserted. The irradiation control circuitry 461 further sets the X-ray intensity (tube voltage, tube current, etc.) to an appropriate level to emit X-rays.

When the irradiation from one direction is completed, the gantry control circuitry 462 rotates the irradiation head unit 412 to the next angle, in this case, the left side of the patient. The irradiation control circuitry 461 adjusts the opening of the multi-leaf collimator again in order to match the shape of the irradiation field of the X-ray to the shape of the tumor. Further, if necessary, a wedge filter or the like for removing the low energy component of the X-ray is inserted. Then, the irradiation control circuitry 461 sets the X-ray intensity at an appropriate level to emit X-rays. This completes one treatment. Treatment is performed several times. The number of treatment is generally 5 to 30 times.

Note that in radiotherapy, since very strong X-rays are emitted, if the tumor position deviates from the X-ray irradiation field, a large adverse effect on the normal tissue is exerted. Therefore, whether the tumor is at the isocenter position or not is verified by the second alignment. There are two verification method. One method is to use X-ray images from two directions and the other is to use cone beam CT (CBCT).

In the former, first, the processing circuitry 464 generates a DRR image based on the CT image for treatment planning, compares the DRR image with the X-ray photographed image to correct the deviation. The DRR image is a pseudo X-ray image generated using a CT image and an X-ray optical system as if the patient imaged by the CT image was captured by the X-ray imaging system. In the latter, CBCT imaging is performed by a CBCT apparatus to generate a CBCT image. The CBCT apparatus may be a single apparatus or may be incorporated in the radiotherapy apparatus 4. The processing circuitry 464 compares the CBCT image with the CT image for treatment planning to correct the positional deviation. Since, with the former, alignment has to be performed primarily based on bones and easy-to-understand organs, positional deviation is often caused in the case of alignment with bone. In addition, when performing alignment based on an easy-to-understand organ, where is no problem when the organ contains a tumor or is in proximity. However positional deviation is likely to occur when the tumor is away from the organ. On the other hand, the CBCT has a merit in that positional deviation is not likely to occur because the organ shape can be clearly depicted. However, since it takes from 30 seconds to 1 minute for CBCT imaging, motion artifacts may be included in the CBCT image, and organ shapes may become unclear or may deviate due to motion artifacts.

As described above, when radiotherapy is performed, the typical operation of the radiotherapy system 1 according to the first embodiment ends.

Here, brief description will be given of the alignment of existing routines. In the existing routine, in the treatment planning stage, a reference point at the time of CT imaging is identified on the patient's body surface, a positional deviation from the reference point to the tumor is measured, and the marker indicating the tumor position is drawn on the body surface from the front and the side based on the body surface. In the treatment stage, rough alignment is performed so that the tumor position matches with the isocenter by matching the marker to the laser sighting instrument installed in the treatment room. Since the marker drawn on this body surface becomes unclear or disappear when the patient enters the bath, it is necessary to rewrite the marker several times in the existing routine. This work may causes errors and is troublesome.

However, according to the first embodiment, the processing circuitry 81 of the treatment support apparatus 8 compares positions between the treatment-time body surface data and the planning-time body surface data included in the planning-time integrated data, and estimates the tumor position of the patient at the time of collection of treatment-time body surface data (that is, radiotherapy stage) based on the position comparison result and the planning-time integrated data. Then, the bed control circuitry 463 of the radiotherapy apparatus 4 moves the treatment top plate 44 so as to match the estimated tumor position to the isocenter.

According to the first embodiment, it is not necessary to draw a marker on the body surface, which is necessary in the existing routine. Accordingly, there is no need to provide a laser sighting instrument in the treatment room. Therefore, according to the first embodiment, it is possible to easily align the patient at the time of radiotherapy comparing with the existing routine. Further, according to the first embodiment, unlike the alignment by a manual operation using sighting instrument or the like, since the position comparison is made between the planning-time body surface data and the treatment-time body surface data by the processing circuitry 81, it is possible to accurately perform the first alignment of the patient at the time of radiotherapy comparing with the existing routine. Further, according to the first embodiment, by collecting the planning-time body surface data only once in the planning stage, it is possible to collect the treatment-time body surface data on a daily basis in the radiotherapy over a plurality of days, and to compare positions between the treatment-time body surface data and the planning-time body surface data. Since the planning-time body surface data, which is the reference of alignment, is not incorrect like a marker, reproducibility of alignment can be enhanced even in radiotherapy over a plurality of days.

Note that in the above embodiment, planning-time integrated data including planning-time body surface data is image-converted in order to match the patient body surface area of the planning-time body surface data to the patient body surface area of the treatment-time body surface data. However, this embodiment is not limited to this. For example, the bed control circuitry 463 of the radiotherapy apparatus 4 may match the patient body surface area of the planning-time body surface data to the patient body surface area of the treatment-time body surface data collected in real time by moving and rotating the treatment top plate 44 with respect to the six axes (X, Y, Z, θx, θy, θz) to coincide with each other. Here, θx, θy, θz indicate the rotation about the X, Y, and Z axes, respectively. Thereby, the position of the body surface of the patient actually placed on the treatment top plate 44 can be matched with the position of the body surface of the patient at the time of planning. Thereafter, the treatment top plate 44 is moved so that the deviation between the position of the current treatment top plate 44 and the isocenter at the present time, the deviation between the reference point of the treatment top plate 44 and the CT reference point, and the deviation between the CT reference point and the tumor position are comprehensively corrected, thereby making it possible to match the tumor position to the isocenter.

Further, in the above embodiment, the planning-time integrated data includes the planning-time body surface data, the medical image data, and the tumor region. However, this embodiment is not limited to this. For example, planning-time integrated data may be integrated data of planning-time body surface data and medical image data, or may be integrated data of planning-time body surface data and tumor region data.

For example, there is medical image data including a tumor region as a recognizable region such as diffusion weighted image data of MR. In this case, the planning-time integrated data may be integrated data of planning-time body surface data and diffusion weighted image data. Tumor region data can be generated by performing image processing on diffusion weighted image data and recognizing or identifying tumor region data.

In the above embodiment, the tumor position automatically matches with the isocenter by automatically moving the treatment top plate 33 based on the amount of positional deviation by the bed control circuitry 463. However, the present embodiment is not limited to this. For example, the amount of positional deviation between the body surface area of the planning-time body surface data and the body surface area of the treatment-time body surface data may be displayed on the display circuitry 85 of the treatment support apparatus 8 or the display circuitry 466 of the radiotherapy apparatus 4. For example, the amount of positional deviation is displayed as a numerical value indicating the distance between the body surface area of the planning-time body surface data and the body surface area of the treatment-time body surface data. Further, the amount of positional deviation may be displayed as a character or graphic indicating the direction of the positional deviation. Alternatively, the amount of positional deviation may be displayed as both the numerical value and the direction.

The display circuitry 85 and the display circuitry 466 are, for example, displays provided in a treatment room or the like. As a result, the user can visually check the amount of positional deviation. While grasping the amount of positional deviation, the user instructs the movement of the treatment top plate 33 via the input circuitry 467. The bed control circuitry 463 can match the tumor position to the isocenter by moving the treatment top plate 33 in accordance with a movement instruction by the user via the input circuitry 467.

In this case, the amount of positional deviation is not limited to be indicated by the display provided in the treatment room. For example, the amount of positional deviation may be indicated by a projector as the display circuitry 85 and the display circuitry 466. The projector projects the amount of positional deviation on the patient placed on the treatment top plate 33. This allows the user to view both the patient and the amount of positional deviation. Therefore, it is possible to more easily grasp the relation between the patient and the amount of positional deviation.

Second Embodiment

In the first embodiment, the planning-time integrated data is image-converted or the treatment top plate 44 is moved so that the patient body surface area of the planning-time body surface data match with the patient body surface area of the treatment-time body surface data respectively. However, this embodiment is not limited to this. In the second embodiment, the position of a patient placed on a treatment top plate 44 is adjusted so that the patient body surface area of the planning-time body surface data and the patient body surface area of the treatment-time body surface data match with each other. Hereinafter, a radiotherapy system 1 according to the second embodiment will be described. Note that in the following description, the same reference numerals denote constituent elements having almost the same functions as those included in the first embodiment, and a repetitive description will be made only when needed.

Figure 11:
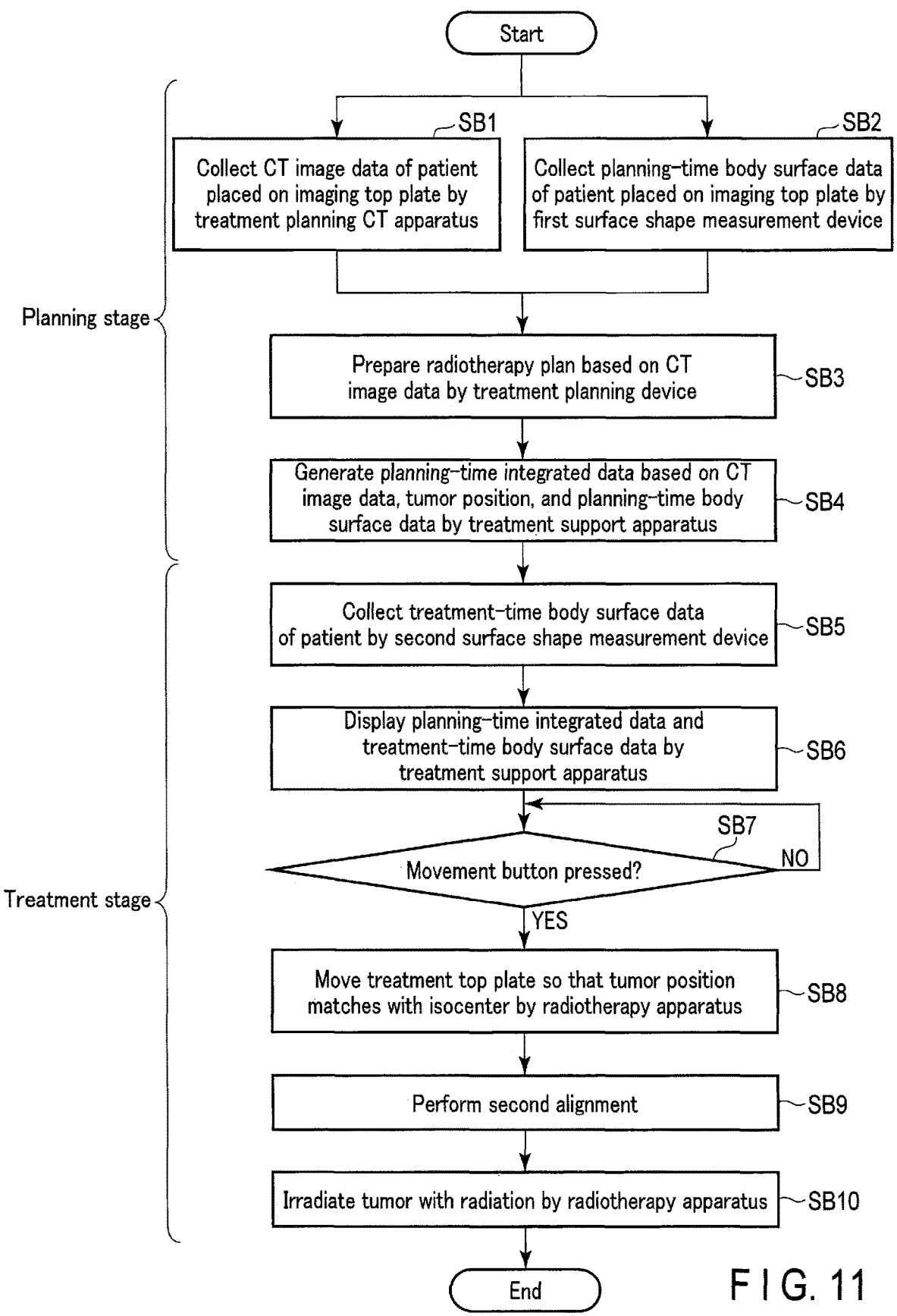
FIG. 11 is a diagram showing a typical flow of the operation of a radiotherapy system according to a second embodiment.

FIG. 11 is a diagram showing a typical flow of the operation of the radiotherapy system 1 according to the second embodiment. Note that since steps SB1 to SB5 in FIG. 11 are the same as steps SA1 to SA5 in FIG. 7, description thereof will be omitted.

When the step SB5 is performed, display circuitry 85 of a treatment support apparatus 8 displays the planning-time integrated data and the treatment-time body surface data (step SB6). More specifically, in step SB6, processing circuitry 81 performs the rendering function 813. In the rendering function 813, the processing circuitry 81 performs rendering on planning-time integrated data to generate a two-dimensional image (hereinafter referred to as a planning-time integrated image), and performs rendering on the treatment-time body surface data to generate a two-dimensional image (hereinafter referred to as a treatment-time body surface image). The planning-time integrated image and the treatment-time body surface image are generated based on the same viewpoint and line of vision. The processing circuitry 81 superimposes the planning-time integrated image and the treatment-time body surface image thus generated, and displays them on the display device of the display circuitry 85.

Figure 12:
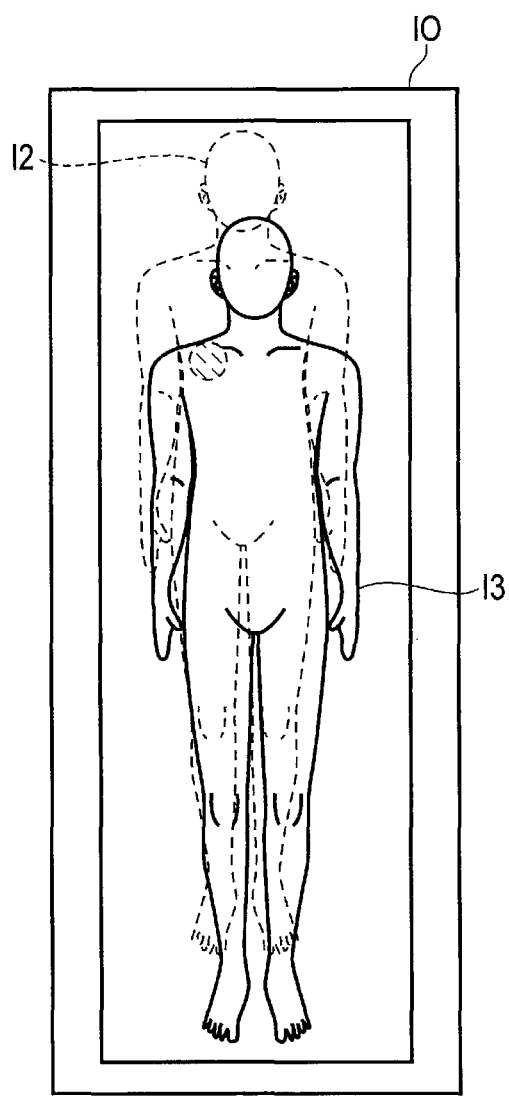
FIG. 12 is a diagram showing an example of a superimposed image of the planning-time integrated image and the treatment-time body surface image displayed in step SB6 in FIG. 11.

FIG. 12 is a diagram showing an example of a superimposed image IO of a planning-time integrated image I2 and a treatment-time body surface image I3. As shown in FIG. 12, the superimposed image IO includes the planning-time integrated image I2 and the treatment-time body surface image I3 superimposed in alignment with each other. The planning-time integrated image I2 may be superimposed on the treatment-time body surface image I3 to be displayed, or the treatment-time body surface image I3 may be superimposed on the planning-time integrated image I2 to be displayed. In order to improve visibility, it is preferable that the image to superimpose is displayed in a translucent manner, and the image to be superimposed is displayed in an opaque state. By displaying the planning-time integrated image I2 and the treatment-time body surface image I3 in a superimposed manner, the amount of positional deviation between the patient body surface area of the planning-time body surface data and the patient body surface area of the treatment-time body surface data can be grasped easily and accurately.

The display device may be, for example, a display provided in a treatment room. As a result, the radiotherapy practician engaged in the treatment room can easily observe the planning-time integrated image I2 and the treatment-time body surface image I3. Further, the display device may be a projector provided on the wall surface of the ceiling of the treatment room or the like. In the case of a projector, the planning-time integrated image I2 and the treatment-time body surface image I3 are superimposed or aligned and are projected onto the body surface of the patient placed on the treatment top plate 44. As a result, the radiotherapy practician engaged in the treatment room can easily observe the planning-time integrated image I2 and the treatment-time body surface image I3.

For example, the processing circuitry 81 may generate a wireframe model of the patient surface area of the planning-time integrated data, generate a solid model of the patient surface area of the treatment-time body surface data, superimpose the wireframe model on the solid model, and displays it on a display circuitry 85. As a result, the display circuitry 85 can clearly distinguish the patient position at the planning stage from the real-time patient position at the treatment stage and display them. Since the patient or radiotherapy practician can clearly distinguish and grasp the position of the patient at the planning stage and the real time position of the patient at the treatment stage, the position of the patient can be easily and accurately adjusted. Therefore, the planning-time integrated data and the treatment-time body surface data can accurately match.

Further, the processing circuitry 81 may convert both the patient surface area of planning-time integrated data and the patient surface area of treatment-time body surface data into a translucent solid model, and the display circuitry 85 may display both of them in different colors. For example, preferably the display circuitry 85 displays the patient surface area of the planning-time integrated data in blue and the patient surface area of the treatment-time body surface data in red. Further, for the sake of simplicity, the display circuitry 85 preferably displays the overlapping area between the patient surface area of planning-time integrated data and the patient surface area of the treatment-time body surface data in green. Further, the display circuitry 85 may display the non-overlapping area between the patient surface area of planning-time integrated data and the patient surface area of the treatment-time body surface data with emphasis in red.

Further, the display circuitry 85 displays the patient surface area of the planning-time integrated data and the patient surface area of the treatment-time body surface data in different colors, may change variously the display mode of planning-time integrated data or treatment-time body surface data in accordance with a matching degree between the patient surface area of the planning-time integrated data and the patient surface area of the treatment-time body surface data. The degree of matching is calculated by a position comparison function 811 of the processing circuitry 81. For example, the processing circuitry 81 counts as the degree of matching the number of pixels or the number of voxels of the overlapping area of the patient surface area of the planning-time integrated data and the patient surface area of the treatment-time body surface data. For example, when the matching degree is lower than a threshold value, the display circuitry 85 preferably displays the patient body surface area of the planning-time integrated data in a blinking manner. In addition, the display circuitry 85 may blink more quickly as the degree of matching is lower, and may slow down the blinking as the degree of matching is higher. In this case, when the patient surface area of the planning-time integrated data and the patient surface area of the treatment-time body surface data perfectly match, the display circuitry 85 terminates the blinking. Alternatively, the display circuitry 85 may display the degree of matching as a numeral or a graph in parallel with the superimposed image of the planning-time integrated image I2 and the treatment-time body surface image I3.

As described above, various display methods are available to match the patient surface area of planning-time integrated data to the patient surface area of the treatment-time body surface data. For example, the radiotherapy practician observes the image displayed on the display circuitry 85, grasps the direction and the distance in which the patient should move in order to match the patient surface area of the planning-time integrated data to the patient surface area of the treatment-time body surface data, and instructs the patient to "Move slightly to the right.", "Rotate the whole body to the right so that the foot becomes straight.", and adjust the position by moving the patient. Alternatively, the patient may observe the image displayed on the display circuitry 85, grasp how much the patient himself is deviated, and correct the deviation by active movement of the patient. In this case, the burden on radiotherapy practician is reduced, which is efficient.

When the step SB6 is performed, the processing circuitry 81 waits until the movement button provided in input circuitry 87 etc. is pressed (step SB7). The patient or radiotherapy practician checks the planning-time integrated data (or planning-time integrated image) displayed in step SB6, changes the patient position and posture based on the data, and matches a position of the patient body surface area of the planning-time body surface data to a position of the patient body surface area of the treatment-time body surface data collected in real time. As a result, the position of the tumor region included in the planning-time integrated data substantially matches with the actual tumor position of the patient.

When matching a position of the patient body surface area of the planning-time body surface data to a position of the patient body surface area of the treatment-time body surface data, the radiotherapy practician presses the movement button provided in the input circuitry 87 etc. (step SB7: YES). When the movement button is pressed, the processing circuitry 81 supplies a signal to a radiotherapy apparatus 4 indicating that the press button has been pressed (hereinafter referred to as a pressed signal).

Upon receiving the supply of the pressed signal, the radiotherapy apparatus 4 moves the treatment top plate 44 so that the tumor position matches with the isocenter of a treatment gantry 41 (step SB8). Specifically, bed control circuitry 463 calculates the distance and direction from the three-dimensional coordinates of the tumor region included in the planning-time integrated data to the three-dimensional coordinates of the isocenter of the treatment gantry 41, and supplies the driving signal according to the calculated distance and direction to a bed drive device 451. The bed drive device 451 receives the supplied driving signal and moves the treatment top plate 44. As a result, the tumor position matches with the isocenter. Note that it is also possible to correct the position of the treatment top plate 44 more precisely by acquiring an X-ray photographed image from two directions or by generating a CBCT image.

When the step SB8 is performed, the radiotherapy apparatus 4 performs the second alignment (step SB9). Since the process of step SB9 is the same as the process of step SA8, a description thereof will be omitted. With the second alignment, more accurate alignment is performed.

When the step SB9 is performed, the radiotherapy apparatus 4 irradiates the tumor of the patient with radiation according to the radiotherapy plan (step SB10). The process of step SB10 is the same as the process of step SA8, and thus the description thereof will be omitted.

When the radiotherapy is performed, the typical operation of the radiotherapy system 1 according to the second embodiment ends.

As described above, the treatment support apparatus 8 according to the second embodiment differs from the treatment support apparatus 8 according to the first embodiment in that positions between planning-time body surface data and treatment-time body surface data are not compared, and by manually adjusting the position of the patient placed on the treatment top plate 44, the patient body surface area of the planning-time body surface data and the patient body surface area of the treatment-time body surface data are made to match indirectly. As a result, even when the position comparison accuracy is not good, the patient body surface area of the planning-time body surface data and the patient body surface area of the treatment-time body surface data can be made to match. As a result, first alignment of the patient at the time of radiotherapy can be easily and accurately performed comparing with existing routines.

Third Embodiment

In radiotherapy, an interference check is performed to simulate the presence or absence of interference between a treatment gantry 41, a treatment bed 42, and a patient. The interference check is performed using a virtual patient model. The body type of the virtual patient model is selected from standard body types less than 50 prepared beforehand, such as standard body type, fat body type, thin body type, or the middle of them. Therefore, a body type of the actual patient and a body type of the virtual patient model may not match in some cases. There is also a case where the position where the patient actually lies on a treatment top plate 44 does not match with the position where the virtual patient model is on the virtual top plate model. Furthermore, as the patient lies on the treatment top plate 44, the treatment top plate 44 may sag due to the influence of the patient's weight. However, it is difficult to simulate this deflection by calculation. Due to the difference between actual result and simulation result, it is difficult to accurately check the interference risk.

Hereinafter, a radiotherapy system 1 according to the third embodiment will be described. In the following description, the same reference numerals denote constituent elements having almost the same functions as those included in the first and the second embodiment, and a repetitive description will be made only when needed.

Figure 13:
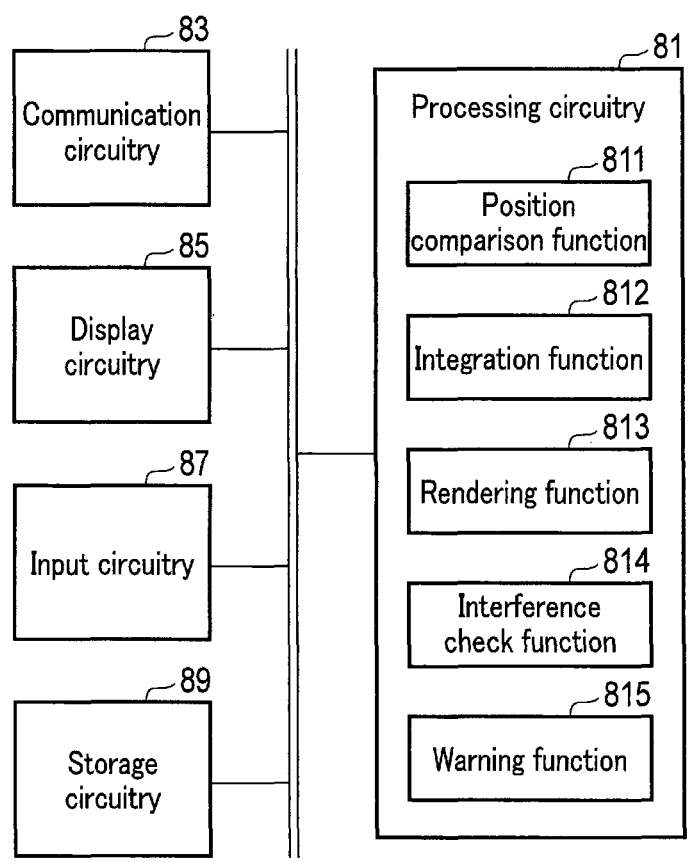
FIG. 13 is a diagram showing the configuration of the treatment support apparatus according to a third embodiment.

FIG. 13 is a diagram showing the configuration of a treatment support apparatus 8 according to the third embodiment. As shown in FIG. 13, processing circuitry 81 of the treatment support apparatus 8 according to the third embodiment performs a position comparison function 811, an integration function 812, a rendering function 813, an interference check function 814, and a warning function 815 at the time of the radiotherapy support.

In the interference check function 814, the processing circuitry 81 determines the presence or absence of interference between the treatment gantry 41, the treatment top plate 44, and the patient based on the simulation of the position and motion of the treatment gantry 41, the treatment top plate 44 and the patient.

In the warning function 815, the processing circuitry 81 issues a warning when it is determined by the interference check function 814 that there is an interference. The warning is performed by, for example, displaying an error message or the like via display circuitry 85, outputting an alarm sound or the like via a speaker (not shown), and the like.

Next, an operation example of the radiotherapy system 1 according to the third embodiment will be described.

Figure 14:
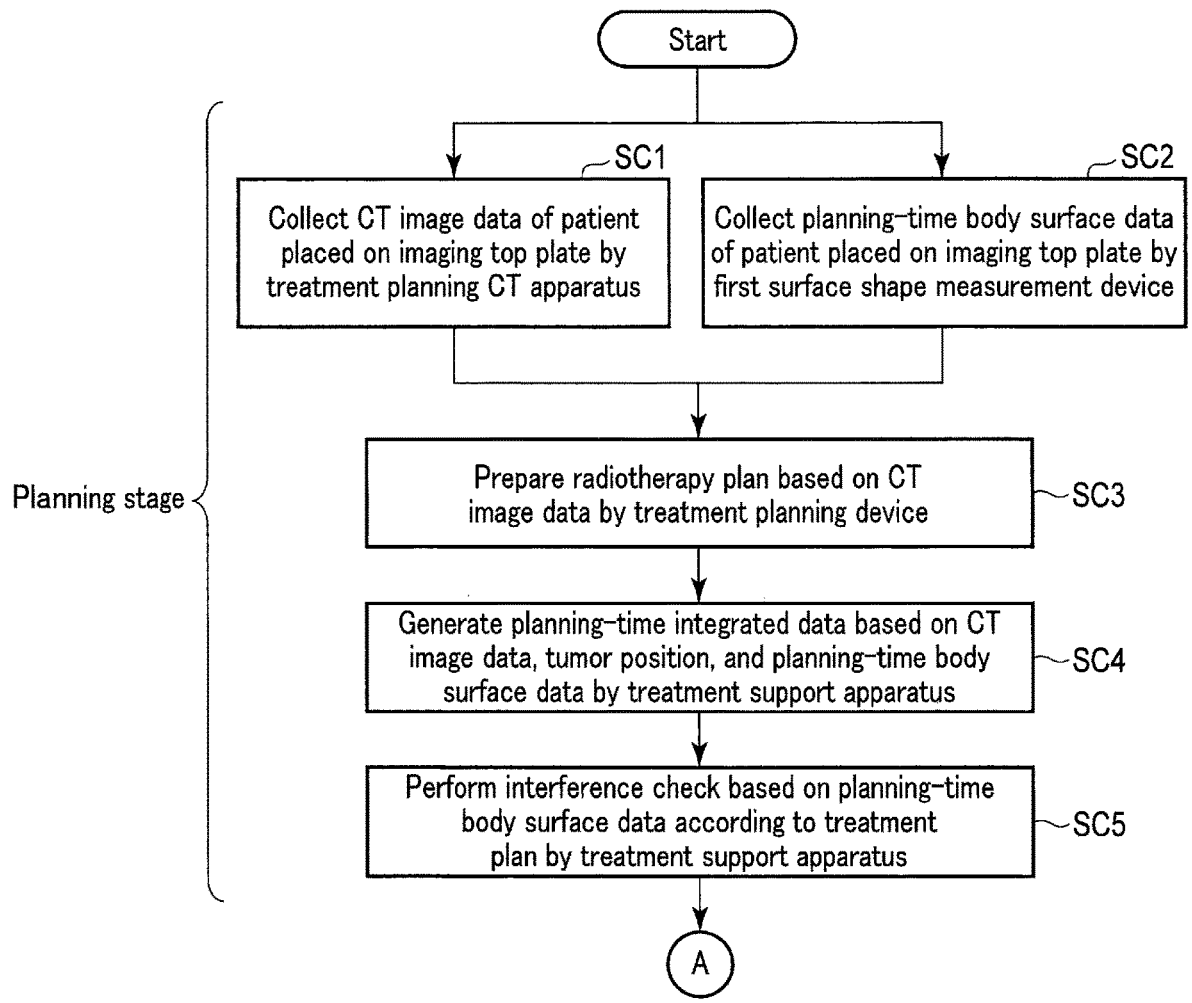
FIG. 14 is a diagram showing a typical flow of the operation of a radiotherapy system according to the third embodiment.
Figure 15:
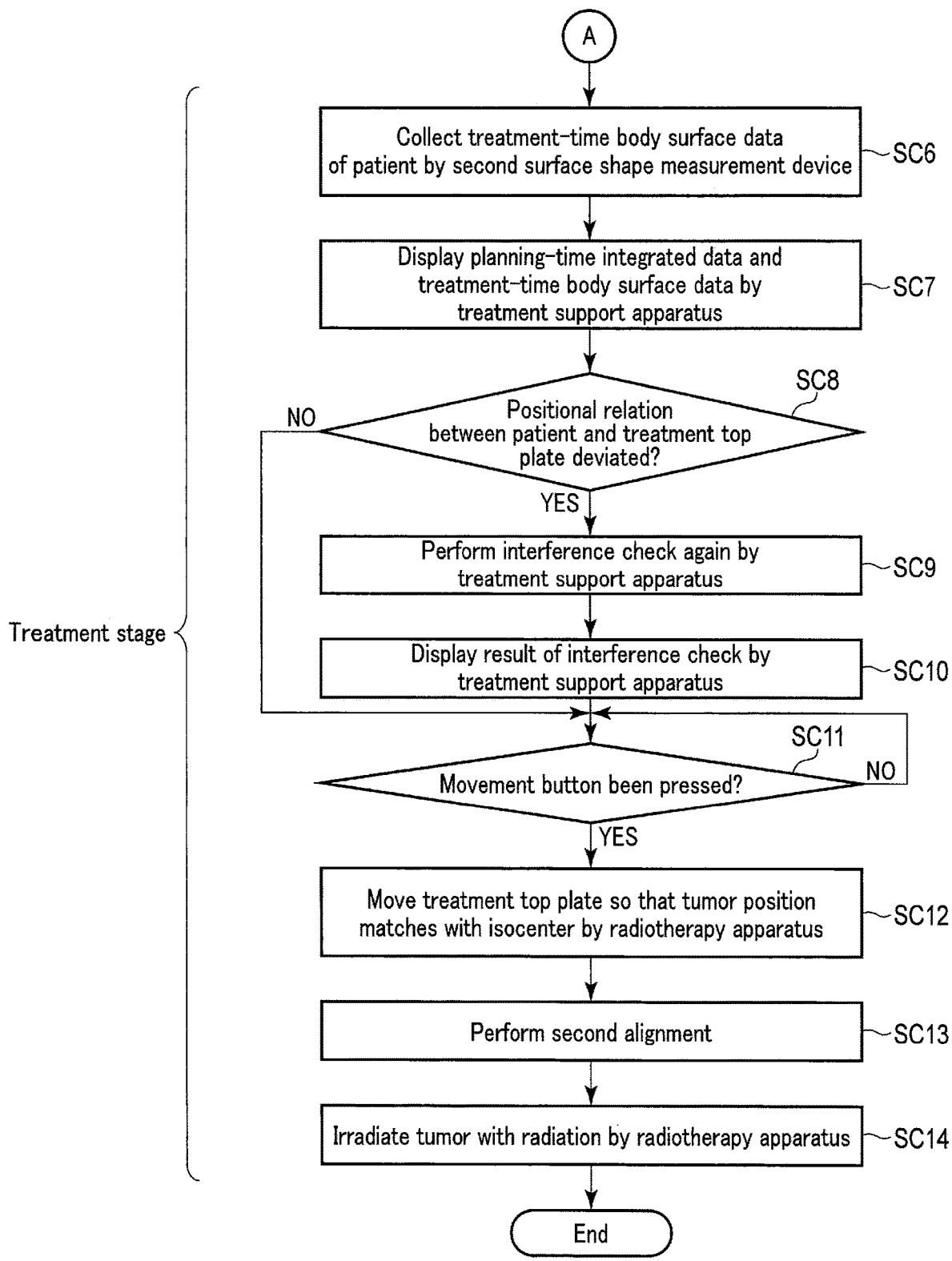
FIG. 15 is a continuation of the flow in FIG. 14.

FIGS. 14 and 15 are diagrams showing a typical flow of the operation of the radiotherapy system 1 according to the third embodiment. Note that since steps SC1 to SC4 in FIG. 14 are the same as steps SB1 to SB4 in FIG. 11, description thereof will be omitted.

When step SC4 is performed, the processing circuitry 81 of the treatment support apparatus 8 performs the interference check function 814 (step SC5). In step S5, the processing circuitry 81 performs interference check according to the radiotherapy plan prepared in step SC3 by using the planning-time body surface data collected in step SC2. For example, the processing circuitry 81 stores in advance information on the structure of the treatment gantry 41 and the treatment bed 42 and information on the movable range of the structure in the storage device or the like. Hereinafter, information on the structure and information on the movable range of the structure will be referred to as mechanism information. The mechanism information can be acquired from the mechanical design data (CAD: Computer-Aided Design) relating to a radiotherapy apparatus 4.

The processing circuitry 81 generates a patient model simulating the body type of the patient based on the patient body surface area included in the planning-time body surface data collected by a first surface shape measurement device 3. That is, in the third embodiment, since the patient model is generated based on the patient body surface area of the planning-time body surface data, not the patient model prepared in advance as a template, it is possible to use a patient model simulating the body type of the actual patient. Further, the processing circuitry 81 generates a top plate model simulating the treatment top plate 44 based on the top plate surface area included in the planning-time body surface data. Note that the top plate surface area included in the planning-time body surface data is a top plate surface area related to an imaging top plate 23. Since the imaging top plate 23 and the treatment top plate 44 are substantially the same shape and material, it is possible to generate a top plate model simulating the treatment top plate 44 based on the top plate surface area included in the planning-time body surface data.

Next, the processing circuitry 81 places the patient model generated based on the planning-time body surface data at an appropriate position of the top plate model assuming that the patient is lying at an appropriate position. When the radiotherapy apparatus 4 is moved in accordance with the radiotherapy plan, the processing circuitry 81 determines whether there is an interference or there is a risk of interfering with proximity between the patient and units of the radiotherapy apparatus 4 (specifically, an irradiation head unit 412, the treatment bed 42, a flat panel detector (FPD) for X-ray imaging, an X-ray tube, etc.).

According to step SC5, it is possible to perform interference check using the patient's accurate body type using the planning-time body surface data collected by the first surface shape measurement device 3. Further, by matching positions where the patient lies on the treatment top plate 44 between a treatment planning CT apparatus 2 and the radiotherapy apparatus 4, it is possible to identify the correct patient position. Further, deflection caused by the patient lying on the treatment top plate 44 can be correctly identified by using the top plate surface area included in the planning-time body surface data. By using such accurate patient model and top plate model, it is possible to perform interference check almost accurately.

In the treatment stage, a second surface shape measurement device 5 collects treatment-time body surface data of the patient (step SC6). Since step SC6 is the same as step SB5, the description is omitted.

When the step SC6 is performed, the display circuitry 85 of the treatment support apparatus 8 displays planning-time integrated data and treatment-time body surface data (step SC7). Since step SC7 is the same as step SB6, the description is omitted. The patient or radiotherapy practician checks the planning-time integrated data displayed in step SC7, changes the position and posture of the patient, and matches a position of the patient body surface area of the planning-time integrated data to a position of the patient body surface area of the treatment-time body surface data.

At this time, the processing circuitry 81 performs the position comparison function 811 (step SC6). In step SC6, the processing circuitry 81 determines whether the positional relation between the patient body surface area and the top plate surface area included in the treatment-time body surface data is deviated from the positional relation between the patient body surface area and the top plate surface area included in the planning-time body surface data by a threshold value or more. The positional relation is defined by, for example, a vector connecting the reference point of the patient body surface area and the reference point of the top plate surface area. The reference point of the patient body surface area and the reference point of the top plate surface area may be set at any positions.

More specifically, the processing circuitry 81 calculates a vector (hereinafter referred to as a treatment-time vector) connecting the reference point of the patient body surface area and the reference point of the top plate surface area included in the treatment-time body surface data, calculates a vector connecting a reference point of the patient body surface area included in the planning-time body surface data and a reference point of the top plate surface area (hereinafter referred to as a planning-time vector), and calculates the difference between the lengths and the difference between the angles of the treatment-time vector and the planning-time vector. Then, the processing circuitry 81 compares the difference in length with the length threshold value, compares the difference in angle with the angle threshold value, and determines whether at least one of the length difference and the angle difference is equal to or larger than the threshold value. When at least one of the length difference and the angle difference is equal to or greater than the threshold value, the processing circuitry 81 determines that the positional relation between the patient and the treatment top plate 44 is deviated (step SC8: YES), the length Is not equal to or greater than the threshold value, the processing circuitry 81 determines that the positional relation between the patient and the treatment top plate 44 is not deviated (step SC8: NO).

Note that the criterion for determining the deviation of the positional relation is merely an example and is not limited to the above. For example, when both the length difference and the angle difference are equal to or greater than the threshold value, the processing circuitry 81 may determine that the positional relation is deviated (step SC8: YES), and may determine that the positional relation is not deviated (step SC8: NO) when at least one of the angular differences is not equal to or greater than the threshold value. Further, the processing circuitry 81 may calculate only one of the length difference and the angle difference of between the treatment-time vector and the planning-time vector. In the case of calculating only the length difference, the processing circuitry 81 compares the length difference with the length threshold value, and when the length difference is equal to or more than the threshold value, may determine that the positional relation is deviated, and when the length difference is not equal to or greater than the threshold value (step SC8: YES), may determine that the positional relation is not deviated (step SC8: NO). In the case of calculating only the angle difference, the determination can be performed in the same way.

When it is determined in step SC8 that the positional relation between the patient and the treatment top plate 44 is deviated (step SC8: YES), the processing circuitry 81 of the treatment support apparatus performs the interference check function 814 (step SC9). In step SC9, the processing circuitry 81 performs interference check again based on the deviation amount of the positional relation (that is, the difference in length and the difference in angle).

When step SC9 is performed, the processing circuitry 81 displays the result of the interference check on the display circuitry 85 (step SC10). In step SC10, the processing circuitry 81 performs the warning function 815. In the warning function 815, when it is determined that the risk of interference is high, the processing circuitry 81 issues a warning to prompt the radiotherapy practician to compensate for the deviation.

When step SC10 is performed or when it is determined in step SC8 that the positional relation between the patient and the treatment top plate 44 is not deviated (step SC8: NO), the processing circuitry 81 waits for the movement button pressed (Step SC11). The patient or the radiotherapy practician checks the planning-time integrated data displayed in step SC7, changes the patient position and posture based on the planning-time integrated data, and matches the planning-time body surface data to the treatment-time body surface data. By matching the treatment-time body surface data collected in real time to the planning-time body surface data included in the planning-time integrated data, the position of the tumor region included in the planning-time integrated data substantially matches with the tumor position of the actual patient.

When matching the treatment-time body surface data to the planning-time body surface data included in the planning-time integrated data, the radiotherapy practician presses a movement button provided in input circuitry 87 or the like (step SC11: YES). When the movement button is pressed, the processing circuitry 81 supplies a pressed signal to the radiotherapy apparatus 4. Upon receiving the supply of the pressed signal, the radiotherapy apparatus 4 moves the treatment top plate 44 so that the tumor position matches with the isocenter of the treatment gantry 41 (step SC12). When the step SC12 is performed, the radiotherapy apparatus 4 performs the second alignment (step SC13). When step SC13 is performed, the radiotherapy apparatus 4 irradiates the patient's tumor with radiation according to the radiotherapy plan (step SC14). Since the process of steps SC12 to SC14 is the same as the process of steps SB8 to SB10, description thereof will be omitted.

When the radiotherapy is performed, the typical operation of the radiotherapy system 1 according to the third embodiment ends.

As described above, in step SC8, the processing circuitry 81 can determine whether the positional relation between the patient and the imaging top plate 23 at the time of planning can accurately reproduce the positional relation between the patient and the treatment top plate 44 at the time of treatment. When the positional relation cannot be accurately reproduced, the interference check is performed again at the previous stage of the radiotherapy as in step SC9. By performing the interference check again, it is possible to reduce the risk of stopping radiotherapy and correcting the treatment plan due to the occurrence of interference at the time of radiotherapy.

Note that when the positional relation between the patient and the imaging top plate 23 at the time of treatment planning can accurately reproduce the positional relation between the patient and the treatment top plate 44 at the time of treatment, steps SC8 to SC10 may not necessarily be performed.

The interference checking function may be improved in order to shorten the time for alignment. Specifically, the processing circuitry 81 enlarges the top plate model by a predetermined margin to generate an enlarged top plate model. The top plate allowable margin is set to an allowable deviation amount of the actual treatment top plate 44 with respect to the imaging top plate 23 at the treatment planning stage. Specifically, the processing circuitry 81 enlarges the patient model by a predetermined margin to generate an enlarged patient model. The patient tolerance margin is set to the allowable deviation amount of the patient at the time of actual treatment with respect to the patient at the treatment planning stage.

The processing circuitry 81 performs interference check based on the enlarged top plate model and the enlarged patient model according to the radiotherapy plan. That is, the processing circuitry 81 determines by simulation whether the treating gantry model, the enlarged top plate model and the enlarged patient model interfere with each other, and when it is determined that they do not interfere with each other, determines that alignment has been completed. When it is determined that there is no interference by the interference check based on such an enlarged model, the determination means that there is a space with a considerable margin between the treatment gantry 41, the treatment bed 42, and the patient. Therefore, it is unnecessary to perform very fine alignment, so that the time required for alignment can be drastically reduced.

On the other hand, the processing circuitry 81 determines that alignment is necessary when it is determined that the treating gantry model, the enlarged top plate model and the enlarged patient model interfere with each other. At this time, the processing circuitry 81 may reduce, automatically or according to the instruction by the radiotherapy practician via the input circuitry 87, the margin of the enlarged top plate model or the enlarged patient model when it is determined that they interfere with each other. The processing circuitry 81 may be reduced to only the portion in which the they are determined to interfere with each other out of the omnidirectional margins of the enlarged top plate model and the enlarged patient model, or may reduce the margin of the enlarged top plate model and the enlarged patient model over all azimuths. In this case, the processing circuitry 81 may reduce both the margin of the enlarged top plate model and the margin of the enlarged patient model, or may reduce either one of them. The processing circuitry 81 performs interference check again using the reduced enlarged top plate model or the reduced enlarged patient model. Even in the case where it is determined from the interference check again that there is no interference, the radiotherapy practician can recognize the risk of interference. In the case where it is determined as a result of the interference check again that there is an interference, the radiotherapy practician will perform the alignment again or restart the radiotherapy plan. In this case, when comparing patient positions in the radiotherapy apparatus 4, it is determined whether the margin is within the allowable margin where the determination is performed using the reduced margin.

Fourth Embodiment

Since radiotherapy is performed over a long period such as 5 weeks or 6 weeks, the body type of a patient may change due to the influence of anticancer drugs and the like. When the body type changes significantly, it is also necessary to prepare the radiotherapy plan again. In the third embodiment, in step SC8, it is determined whether interference checking should be performed again according to the positional relation between the patient and the treatment top plate 44. However, since the change in the body type of the patient is not reflected in the positional relation between the patient and a treatment top plate 44, even when the body type greatly changes, the interference check may not be performed again.

Hereinafter, a radiotherapy system 1 according to the fourth embodiment will be described. In the following description, the same reference numerals denote constituent elements having almost the same functions as those included in the first, the second and the third embodiment, and a repetitive description will be made only when needed.

Figure 16:
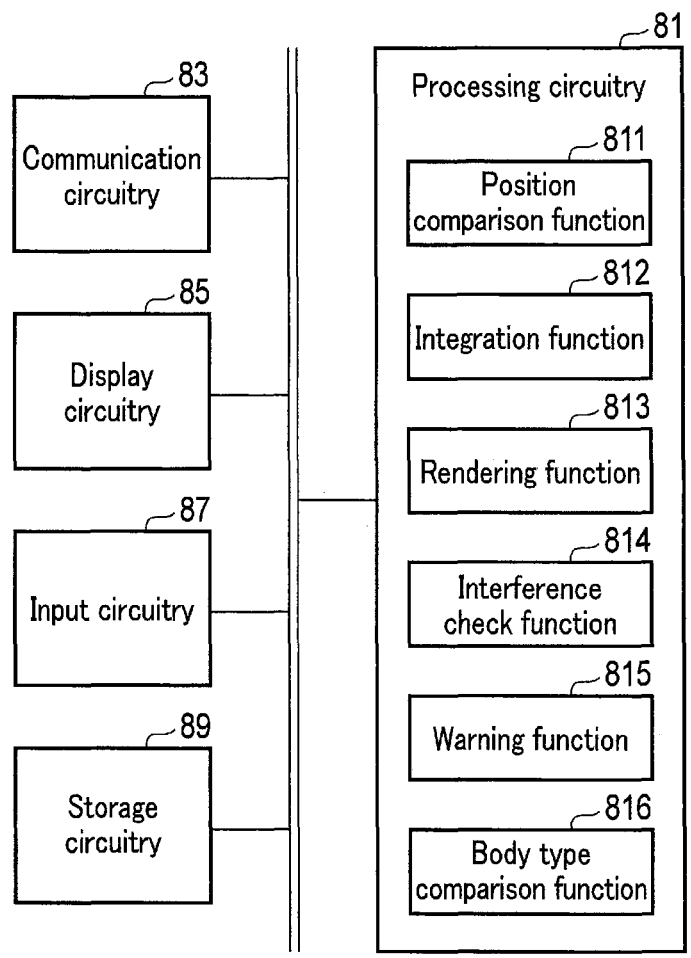
FIG. 16 is a diagram showing the configuration of a treatment support apparatus according to a fourth embodiment.

FIG. 16 is a diagram showing the configuration of the treatment support apparatus according to the fourth embodiment. As shown in FIG. 16, processing circuitry 81 of the treatment support apparatus according to the fourth embodiment performs a position comparison function 811, an integration function 812, a rendering function 813, an interference check function 814, a warning function 815, and a body type comparison function 816 at the time of the radiotherapy support.

In the body type comparison function 816, the processing circuitry 81 compares the body type of the patient at the planning stage with the body type of the patient at the treatment stage. In the present embodiment, the distance interval in the vertical direction of the patient body surface area included in the planning-time body surface data and the treatment-time body surface data is regarded as the body type. In other words, the processing circuitry 81 compares the distance interval in the vertical direction of the patient body surface area of the planning-time body surface data with the distance interval in the vertical direction of the patient body surface area of the treatment-time body surface data. Further, the processing circuitry 81 may compare the weight of the patient measured by the body weight sensor or the like in the planning stage with the weight of the patient measured by the body weight sensor or the like in the treatment stage. The body weight sensors are provided on an imaging bed 22 and a treatment bed 42. The data of the body weight measured by the body weight sensor is transmitted to a treatment support apparatus 8.

Next, an operation example of the radiotherapy system 1 according to the fourth embodiment will be described. Since the flow of the operation of the radiotherapy system 1 according to the third embodiment is substantially the same as the flow of the operation of the radiotherapy system 1 according to the third embodiment, description will be made using FIG. 14 and FIG. 15.

In step SC2 in the planning stage, a first surface shape measurement device 3 collects the planning-time body surface data of the patient placed on an imaging top plate 23 of a treatment planning CT apparatus 2. At this time, the body weight of the patient at the time of collecting the planning-time body surface data is measured by the body weight sensor provided in the imaging bed 22. The data of the body weight measurement value is supplied to the treatment support apparatus 8.

In step SC6 in the treatment stage, a second surface shape measurement device 5 collects the treatment-time body surface data of the patient placed on the treatment top plate 44 of the radiotherapy apparatus 4. At this time, the body weight of the patient at the time of collecting the treatment-time body surface data is measured by the body weight sensor provided in the treatment bed 42. The data of the body weight measurement value is supplied to the treatment support apparatus 8.

Note that although the body weight sensor is provided in the imaging bed 22 and the treatment bed 42, the present embodiment is not limited to this. For example, a body weight sensor may be provided at the entrance of the planning room and the treatment room, or a body weight sensor may be provided in the dressing room or at the entrance of the dressing room.

When the step SC6 is performed, the display circuitry 85 of the treatment support apparatus 8 displays planning-time integrated data and treatment-time body surface data (step SC7). Since step SC7 is the same as step SB6, the description is omitted. The patient or radiotherapy practician checks the planning-time integrated data displayed in step SC7, changes the position and posture of the patient, and matches a position of the patient body surface area of the planning-time integrated data to a position of the patient body surface area of the treatment-time body surface data.

At this time, the processing circuitry 81 performs the position comparison function 811 (step SC6). In step SC6, the processing circuitry 81 determines whether the positional relation between the patient body surface area and the top plate surface area included in the treatment-time body surface data is deviated from the positional relation between the patient body surface area and the top plate surface area included in the planning-time body surface data by a threshold value or more.

In step SC6, the processing circuitry 81 performs the body type comparison function 816 in parallel with the execution of the position comparison function 811.

Figure 17:
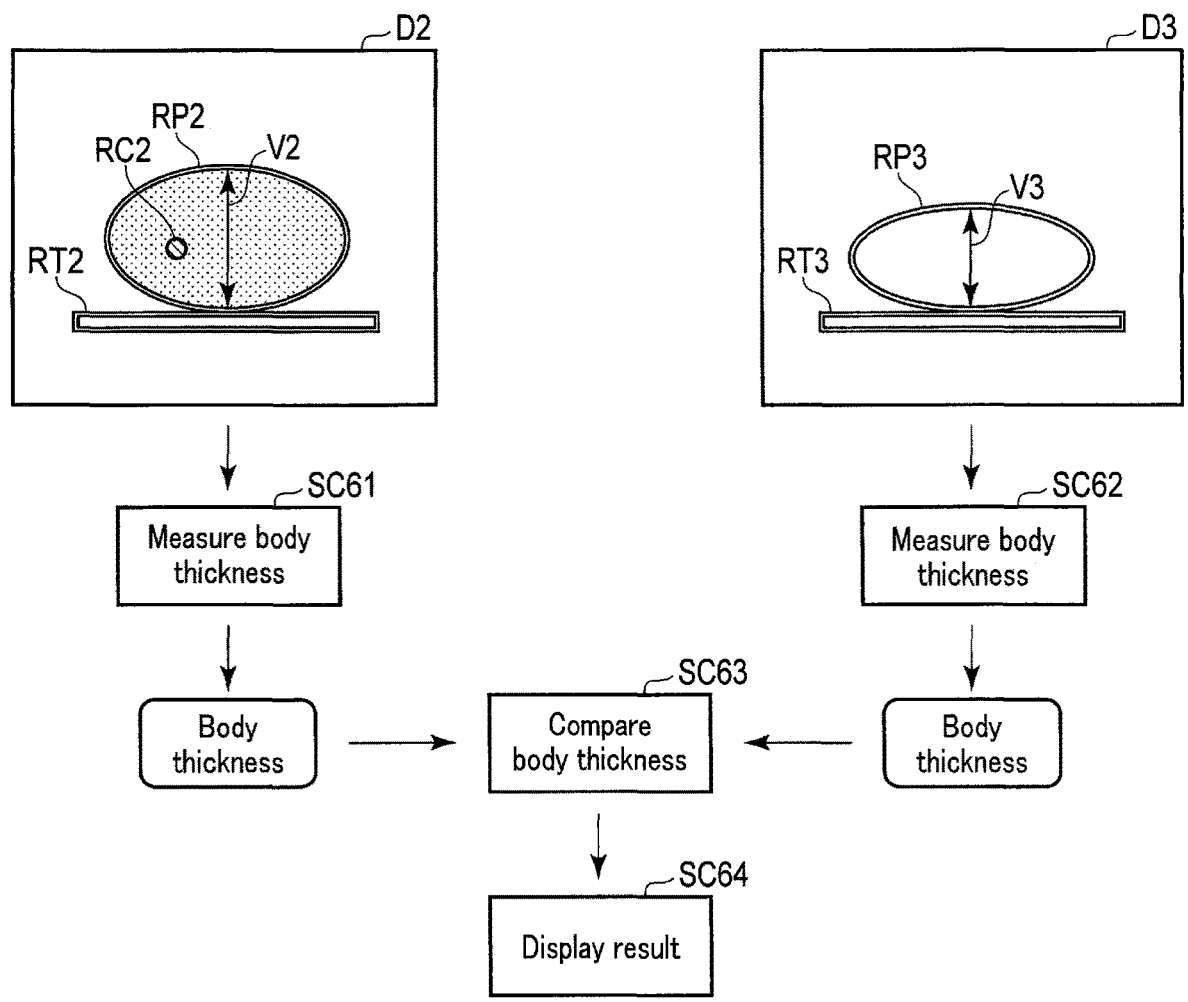
FIG. 17 is a diagram schematically showing a process using the body type comparison function of processing circuitry according to the fourth embodiment.

FIG. 17 is a diagram schematically showing a process by the body type comparison function 816 of the processing circuitry 81. As shown in FIG. 17, first, the processing circuitry 81 reads the planning-time integrated data D2 and the treatment-time body surface data D3 relating to a predetermined axial section. The planning-time integrated data D2 includes a patient body surface area RP2 included in the planning-time body surface data, a top plate surface area RT2 included in the planning-time body surface data, and a tumor region RC2 included in CT image data ICT2. The treatment-time body surface data D3 includes the patient body surface area RP3 included in the treatment-time body surface data and a top plate surface area RT3 included in the treatment-time body surface data.

As shown in FIG. 16, the processing circuitry 81 performs a body thickness measuring process on the planning-time integrated data D2 (step SC61). In step SC61, the processing circuitry 81 measures a distance interval V2 in the vertical direction of the patient body surface area RP2 as a body thickness. Note that the vertical direction refers to a direction perpendicular to the surface of the imaging top plate 23. Similarly, the processing circuitry 81 performs the body thickness measuring process on the treatment-time body surface data D3 (step SC62). In step SC62, the processing circuitry 81 measures a distance interval V3 in the vertical direction of the patient body surface area RP3 as a body thickness.

When steps SC61 and SC62 are performed, the processing circuitry 81 performs a body thickness comparison process (step SC63). In step SC63, the processing circuitry 81 compares a body thickness value V2 at the time of planning measured at step SC61 with a body thickness value V3 at the time of treatment measured at step SC62. More specifically, the processing circuitry 81 calculates the difference between the body thickness value V2 at the time of planning and the body thickness value V3 at the time of treatment, and determines whether the difference is within a predetermined allowable range, that is, determines whether replanning is required. When the difference is not within the permissible range, it is better to carry out the radiotherapy plan again because the physical structure of the patient has largely changed between the time of planning and the time of treatment. When the difference falls within the allowable range, since the physical structure of the patient has not changed so much between the time of planning and the time of treatment, it is not necessary to carry out the radiotherapy plan again.

When the step SC63 is performed, the processing circuitry 81 displays the result of the body thickness comparison in the step SC63 on the display circuitry 85 (step SC64). Here, when the difference between the body thickness value V2 at the time of planning and the body thickness value V3 at the time of treatment is not within the allowable range, the processing circuitry 81 performs the warning function 815. In the warning function 815, the processing circuitry 81 issues a warning stating that the physical structure of the patient has largely changed between the time of planning and the time of treatment. For example, the processing circuitry 81 transmits a warning signal to the radiotherapy apparatus 4. Upon receipt of the warning signal, processing circuitry 464 of the radiotherapy apparatus 4 displays on a display 466 provided in the treatment room a message to the radiotherapy practician stating that "The patient's body type is greatly changed". A warning message stating that "Replanning may be required." is displayed.

Furthermore, the processing circuitry 464 displays a verification button together with a warning message. After completing the replanning, the radiotherapy practician will press the verification button. Preferably, after radiotherapy is once cancelled, the CT image for radiotherapy is prepared again, the radiotherapy plan is carried out again, and so forth. Then, radiotherapy is resumed. In this case, the verification button is pressed. When the verification button is pressed, the processing circuitry 464 notifies the irradiation control circuitry 461 of permission of emitting the radiation (X-ray). In the case where irradiation is instructed when permission of irradiation is notified, the irradiation control circuitry 461 can emit the radiation. In other words, the processing circuitry 464 limits emission of the radiation unless the verification button is pressed.

Instead of the body thickness, the processing circuitry 81 may compare the body weights measured by the body weight sensor. Specifically, the processing circuitry 81 calculates the difference between the weight at the time of planning and the weight at the time of treatment, and determines whether the difference is within a predetermined allowable range, that is, whether the replanning is required. As in the case of comparing body thicknesses, the processing circuitry 81 issues a warning because the physical structure of the patient has largely changed between the time of planning and the time of treatment when the difference with respect to the body weight is not within the allowable range. When the difference falls within the allowable range, since the physical structure of the patient has not changed so much between the time of planning and the time of treatment, it is not necessary to carry out the radiotherapy plan again.

It should be noted that the processing circuitry 81 may determine whether the replanning is required by using both the difference with respect to the body thickness and the difference with respect to the body weight. For example, when either one of the difference with respect to the body thickness and the difference with respect to the body weight is not within the allowable range, preferably the processing circuitry 81 may determine that the replanning is required and issue a warning. On the other hand, when both of the difference with respect to the body thickness and the difference with respect to the body weight are within the allowable range, the processing circuitry 81 determines that the replanning is not required. By using both the difference with respect to the body thickness and the difference with respect to the body weight as described above, it is possible to accurately determine whether the replanning is required.

When it is determined that the replanning is required, the processing circuitry 81 performs steps SC9 and SC10. When it is determined that the replanning is not required or step SC10 is performed, the processing circuitry 81 performs steps SC11, SC12, SC13 and SC14.

When radiotherapy is performed in step SC13, the typical operation of the radiotherapy system 1 according to the fourth embodiment ends.

Note that in the above-described step SC63, the difference regarding the body thickness is calculated using the planning-time body surface data and the treatment-time body surface data. However, this embodiment is not limited to this. For example, under the condition that the imaging top plate 23 or the treatment top plate 44 are positioned at the same height, the processing circuitry 81 aligns, by the position comparison function 811, the planning-time body surface data with the treatment-time body surface data. Specifically, the planning-time integrated data or the planning-time body surface data is image-converted so that the patient body surface area of the planning-time body surface data matches with the patient body surface area of the treatment-time body surface data. Then, the processing circuitry 81 calculates by the body type comparison function 816 the positional deviation amount in the vertical direction between the planning-time body surface data and the treatment-time body surface data after alignment as a difference with respect to the body thickness. As a result, it is possible to calculate a more accurate difference with respect of body thickness. In this case, as in the above-described step SC64, the processing circuitry 81 preferably issues a warning stating that the physical structure of the patient has largely changed between the time of planning and the time of treatment when the difference regarding the body thickness is not within the allowable range. As a result, a warning can be issued based on more accurate information, the reliability of the warning can be improved, and the efficiency of radiotherapy can be improved.

Applied Example

In the above embodiment, information such as planning-time integrated data and positional deviation amount is displayed by the display circuitry 85 of the treatment support apparatus 8. However, information such as planning-time integrated data and positional deviation amount according to the present embodiment may be displayed on a head mounted display attached to a user such as a radiotherapy practician.

FIG. 18 is a diagram showing the configuration of the information display system according to the applied example. The information display system is incorporated in the radiotherapy system 1. As shown in FIG. 18, a head mounted display 9 is a display device mounted on the user's head. For example, as shown in FIG. 18, the head mounted display 9 is a glasses type display device.

The head mounted display 9 includes a left eye lens 91 and a right eye lens 92. The left eye lens 91 and the right eye lens 92 are supported by a frame 93 such as a temple. The frame 93 is provided with a display 94, a position detector 95, and a communication interface 96.

For example, the display 94 is provided on the frame 93 so as to be positioned in front of the left eye lens 91. The display 94 is implemented by, for example, a combination of a translucent screen and a projector that projects an image on the screen.

The position detector 95 may be any position sensor such as a global positioning system (GPS) sensor, magnetic sensor, an electric sensor, and the like. When detecting only the position of the head mounted display 9, the number of the position detector 95 may be one, and it may be provided at any position. However, when detecting the position and direction of the head mounted display 9, they are provided on the left side and the right side of the head mounted display 9. The direction is calculated based on the relative relationship of the position of each position detector 95. The direction substantially matches with the direction of the line of sight of the user wearing the head mounted display 9. The line-of-sight direction may be calculated by a processor such as a CPU (not shown) provided on the head mounted display 9 or by the processing circuitry 81 of the treatment support apparatus 8. Hereinafter, the position and the line-of-sight direction are collectively referred to as position information.

The communication interface 96 communicates information with the treatment support apparatus 8. For example, the communication interface 96 transmits the position information to the treatment support apparatus 8, and receives the display integrated data from the treatment support apparatus 8.

For example, at the time of alignment at the treatment stage, the user wears the head mounted display 9. The position detector 95 of the head mounted display 9 repeatedly detects the position and the line-of-sight direction of the position detector 95 and repeatedly transmits the position information to the treatment support apparatus 8. The processing circuitry 81 of the treatment support apparatus 8 converts the planning-time integrated data into display integrated data having a format for displaying the planning-time integrated data on the head mounted display 9 in the rendering function 813. Specifically, the processing circuitry 81 generates rendering image data (display integrated data) of planning-time integrated data on the head mounted display 9 as a viewpoint based on the planning-time integrated data and position information. More specifically, planning-time integrated data is arranged in the three-dimensional image space, and a viewpoint is set at the position of the head mounted display 9 in the three-dimensional image space. For example, planning-time integrated data is arranged at a treatment location defined in a three dimensional image space. The treatment position is defined in a region including at least the tumor position. A ray passing through planning-time integrated data is set along the line-of-sight direction from the viewpoint, and volume rendering based on the ray is performed. As a result, the rendered image data (display integrated data) relating to the integrated data on which the viewpoint is set on the head mounted display 9 is generated. The display integrated data is, for example, displayed translucently. As a result, it is possible to visually recognize the actual patient, the treatment top plate 44, and the like which are superimposed on the display integrated data.

As described above, according to the applied example, it is possible to provide a system as if the patient represented by planning-time integrated data is lying on the treatment top plate 44. Since the display integrated data is based on planning-time integrated data, in addition to the patient body surface data, the tumor position is also depicted. The user can move the treatment top plate 44 so that the translucent display integrated data and the body surface of the patient observed through the display integrated data match with each other. The user can be caused to move the treatment top plate 44 so that the tumor position depicted in the display integrated data matches with the isocenter. In this way, it is possible to accurately and conveniently perform the first alignment of the patient.

It should be noted that the planning-time integrated data may be displayed on the head mounted display 9. That is, in the treatment stage, the processing circuitry 81 of the treatment support apparatus 8 may transmit planning-time integrated data to the head mounted display 9, and the head mounted display 9 may display the received planning-time integrated data. In this case, it is unnecessary for the head mounted display 9 to be provided with the position detector 95.

Thus, according to at least one of the embodiments described above, it is possible to accurately and conveniently perform the first alignment of the patient at the time of radiotherapy.

The combination of the processor and the memory according to the present embodiment may be implemented by an application specific integrated circuit (ASIC), a field programmable gate array (FPGA), a complex programmable logic device (CPLD), or a simple programmable logic device (SPLD).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A radiotherapy system comprising:
a medical image diagnostic apparatus configured to collect medical three-dimensional image data of a patient at a time of treatment planning;
a first body surface data collecting device configured to collect first body surface data representing a three-dimensional body surface of the patient at the time of treatment planning; and
processing circuitry configured to generate integrated data including a mark indicating a tumor position of the patient that is identified in the medical three-dimensional image data and the first body surface data by integrating coordinates respectively defining the medical three-dimensional image data and the first body surface data into an identical three-dimensional coordinate system.

2. The radiotherapy system according to claim 1, further comprising:
a display device;
a treatment bed that comprises a treatment top plate and that is configured to movably support the treatment top plate on which the patient is placed; and
a radiotherapy gantry configured to irradiate the patient with radiation,
wherein the processing circuitry is further configured to arrange the integrated data at a treatment position and display the integrated data arranged at the treatment position on the display device.

3. The radiotherapy system according to claim 2,
wherein the display device is a head mounted display,
wherein the head mounted display includes a position detector,
wherein the processing circuitry is further configured to set a viewpoint on the head mounted display based on a position detected by the position detector, and generate display integrated data arranged at the treatment position, and
wherein the head mounted display is configured to display the display integrated data.

4. The radiotherapy system according to claim 2, further comprising:
a second body surface data collecting device configured to collect second body surface data representing a three-dimensional body surface of the patient placed on the treatment top plate,
wherein the processing circuitry is further configured to generate combined data of the integrated data arranged at the treatment position and the second body surface data, and display the combined data on the display device.

5. The radiotherapy system according to claim 4, further comprising:
bed control circuitry configured to control a movement of the treatment top plate so that the mark indicating the tumor position included in the integrated data matches with an isocenter of the radiotherapy gantry.

6. The radiotherapy system according to claim 5, wherein the bed control circuitry is further configured to determine a control parameter of the treatment bed so that the first body surface data and the second body surface data both of which are included in the integrated data match with each other, and control the movement of the treatment top plate based on the control parameter.

7. The radiotherapy system according to claim 6, wherein the processing circuitry is further configured to calculate a positional deviation amount between a body surface of the patient at the time of treatment planning represented by the first body surface data included in the integrated data and a body surface of the patient placed on the treatment top plate represented by the second body surface data, and wherein the display device is configured to display information representing the positional deviation amount.

8. The radiotherapy system according to claim 7, wherein the display device includes a projector configured to project information representing the positional deviation amount onto the treatment top plate or the patient placed on the treatment top plate.

9. The radiotherapy system according to claim 7, wherein the display device includes a display provided at a position visible to the patient placed on the treatment top plate in a room in which the treatment bed is installed.

10. The radiotherapy system according to claim 7, wherein
the medical image diagnostic apparatus includes an imaging bed,
the imaging bed includes an imaging top plate, and movably supports the imaging top plate, and
the processing circuitry is further configured to calculate, as the positional deviation amount, a first deviation amount relating to a position between the first body surface data and the second body surface data within a plane parallel to the imaging top plate and the treatment top plate when the imaging top plate and the treatment top plate are positioned at a same height.

11. The radiotherapy system according to claim 10, wherein the processing circuitry is further configured to calculate a second deviation amount between a body type of the patient at a time of collecting the first body surface data and a body type of the patient at a time of collecting the second body surface data.

12. The radiotherapy system according to claim 11,
wherein the processing circuitry is further configured to:
align the first body surface data with the second body surface data in a case where the imaging top plate and the treatment top plate are positioned at a same height, and
calculate, as the second deviation amount, a positional deviation in a direction perpendicular to the imaging top plate and the treatment top plate between the first body surface data and the second body surface data after the processing circuitry aligns the first body surface data with the second body surface data.

13. The radiotherapy system according to claim 11, wherein the processing circuitry is further configured to issue a warning when the second deviation amount exceeds a threshold value.

14. The radiotherapy system according to claim 7, wherein the processing circuitry is further configured to perform an interference check under a calculation condition that a patient model simulating the patient lies in an appropriate position on a top plate model simulating the treatment top plate.

15. The radiotherapy system according to claim 14, wherein the processing circuitry is further configured to check a presence or an absence of a mechanical interference between the patient model, the top plate model, and a radiotherapy gantry model simulating the radiotherapy gantry.

16. The radiotherapy system according to claim 14, wherein the processing circuitry is further configured to use an enlarged patient model larger than the patient as the patient model, and use an enlarged top plate model larger than the treatment top plate as the top plate model.

17. The radiotherapy system according to claim 14, wherein the processing circuitry is further configured to perform an interference check again based on the second body surface data and the positional deviation amount when the positional deviation amount between the first body surface data and the second body surface data is larger than a predetermined value.

18. The radiotherapy system according to claim 1, wherein the processing circuitry is further configured to attach the mark indicating the tumor position of the patient in the medical three-dimensional image data, and a coordinate defining the mark is integrated into the identical three-dimensional coordinate system by integrating the coordinates respectively defining the medical three-dimensional image data and the first body surface data into the identical three-dimensional coordinate system.

19. The radiotherapy system according to claim 1, further comprising a second body surface data collecting device configured to collect second body surface data representing a three-dimensional body surface of the patient at a time of a radiotherapy treatment,
wherein the processing circuitry is further configured to match the first body surface data included in the integrated data to the second body surface data, and specify, based on the mark indicating the tumor position of the patient included in the integrated data, three-dimensional coordinates of the tumor position of the patient.

20. The radiotherapy system according to claim 1, wherein the processing circuitry is further configured to generate the integrated data including the medical three-dimensional image data of the patient, the mark indicating the tumor position of the patient that is identified in the medical three-dimensional image data, and the first body surface data by integrating coordinates respectively defining the medical three-dimensional image data, the mark indicating the tumor position, and the first body surface data into the identical three- dimensional coordinate system.

21. A treatment support apparatus comprising:
processing circuitry configured to generate integrated data including a mark indicating a tumor position of a patient that is identified in a medical three-dimensional image data of the patient at a time of treatment planning in radiotherapy and first body surface data representing a three-dimensional body surface of the patient at the time of treatment planning by integrating coordinates respectively defining the medical three-dimensional image data and the first body surface data into an identical three-dimensional coordinate system.

22. The treatment support apparatus according to claim 21, wherein the processing circuitry is further configured to attach the mark indicating the tumor position of the patient in the medical three-dimensional image data, and a coordinate defining the mark is integrated into the identical three-dimensional coordinate system by integrating the coordinates respectively defining the medical three-dimensional image data and the first body surface data into the identical three-dimensional coordinate system.

23. The treatment support apparatus according to claim 21, wherein the processing circuitry is further configured to acquire second body surface data representing a three-dimensional body surface of the patient at a time of a radiotherapy treatment, match the first body surface data included in the integrated data to the second body surface data, and specify, based on the position of the tumor region of the patient included in the integrated data three-dimensional coordinates of the position of the tumor region of the patient in the medical three-dimensional image data of the patient.

24. The treatment support apparatus according to claim 21, wherein the processing circuitry is further configured to generate the integrated data including the medical three-dimensional image data of the patient, the mark indicating the tumor position of the patient that is identified in the medical three-dimensional image data, and the first body surface data by integrating coordinates respectively defining the medical three-dimensional image data, the mark indicating the tumor position, and the first body surface data into the identical three-dimensional coordinate system.

\* \* \* \* \*